US010231476B2

(12) United States Patent
Baniel et al.

(10) Patent No.: US 10,231,476 B2
(45) Date of Patent: Mar. 19, 2019

(54) SWEETENER COMPOSITIONS AND FOODS, BEVERAGES, AND CONSUMABLE PRODUCTS MADE THEREOF

(71) Applicant: DOUXMATOK LTD, Tel-Aviv (IL)

(72) Inventors: Avraham Baniel, Jerusalem (IL); Michael Zviely, Haifa (IL); Shay Eliyahu, Tel-Aviv (IL); Noa Gelbart, Herzliya (IL); Eran Baniel, Tel-Aviv (IL); Ronit Romm, Jerusalem (IL); Nadine Magal Santana, D.N. Hefer (IL); Alexander Trachtenberg, Ramat-Gan (IL); Yael Miriam Har-Tal Eliyahu, Tel-Aviv (IL)

(73) Assignee: DouxMatok Ltd, Tel-Aviv (IL)

(*) Notice: Subject to any disclaimer, the term of this patent is extended or adjusted under 35 U.S.C. 154(b) by 0 days.

(21) Appl. No.: 15/222,916

(22) Filed: Jul. 28, 2016

(65) Prior Publication Data

US 2016/0331012 A1 Nov. 17, 2016
US 2017/0280758 A9 Oct. 5, 2017

Related U.S. Application Data

(63) Continuation of application No. PCT/IB2015/001153, filed on Apr. 3, 2015, and a continuation-in-part of application No. 14/629,272, filed on Feb. 23, 2015.

(60) Provisional application No. 62/140,299, filed on Mar. 30, 2015, provisional application No. 61/975,683, filed on Apr. 4, 2014, provisional application No. 62/042,154, filed on Aug. 26, 2014, provisional application No. 62/074,518, filed on Nov. 3, 2014.

(51) Int. Cl.
| | |
|---|---|
| *A23L 27/30* | (2016.01) |
| *A61Q 11/00* | (2006.01) |
| *A61K 8/60* | (2006.01) |
| *A61K 8/25* | (2006.01) |
| *A23L 29/00* | (2016.01) |
| *A23L 29/30* | (2016.01) |
| *A61K 47/02* | (2006.01) |
| *A61K 47/26* | (2006.01) |
| *A23L 2/60* | (2006.01) |
| *A61K 47/00* | (2006.01) |

(52) U.S. Cl.
CPC ............... *A23L 27/34* (2016.08); *A23L 2/60* (2013.01); *A23L 27/33* (2016.08); *A23L 29/015* (2016.08); *A23L 29/30* (2016.08); *A23L 29/37* (2016.08); *A61K 8/25* (2013.01); *A61K 8/60* (2013.01); *A61K 47/00* (2013.01); *A61K 47/02* (2013.01); *A61K 47/26* (2013.01); *A61Q 11/00* (2013.01); *A61K 2800/10* (2013.01)

(58) Field of Classification Search
CPC ........ A23L 29/015; A23L 29/30; A23L 29/37; A61K 8/25
See application file for complete search history.

(56) References Cited

U.S. PATENT DOCUMENTS

| | | |
|---|---|---|
| 3,175,299 A | 3/1965 | Boucher |
| 3,503,803 A | 3/1970 | Richard et al. |
| 3,655,578 A * | 4/1972 | Yates ............... C01B 33/1435 516/83 |
| 3,988,162 A | 10/1976 | Wason |
| 4,016,337 A | 4/1977 | Hsu |
| 4,021,582 A | 5/1977 | Hsu |
| 4,343,820 A | 8/1982 | Roseman |
| 4,513,012 A | 4/1985 | Carroll et al. |
| 4,626,287 A | 12/1986 | Shah et al. |
| 4,659,388 A | 4/1987 | Innami et al. |
| 4,671,823 A | 6/1987 | Shah et al. |
| 4,774,099 A | 9/1988 | Feeney et al. |
| 4,925,693 A | 5/1990 | Lauly |
| 4,976,972 A | 12/1990 | Patel et al. |
| 4,981,698 A | 1/1991 | Cherukuri et al. |
| 5,133,977 A | 7/1992 | Patel |
| 5,145,707 A | 9/1992 | Lee |
| 5,252,136 A | 10/1993 | Desforges et al. |
| 5,260,091 A | 11/1993 | Locke et al. |
| 5,266,335 A | 11/1993 | Cherukuri et al. |
| 5,314,810 A | 5/1994 | Kono et al. |
| 5,411,730 A | 5/1995 | Kirpotin et al. |
| 5,492,814 A | 2/1996 | Weissleder |
| 5,603,920 A * | 2/1997 | Rice .................. A61K 8/25 423/335 |
| 5,651,958 A * | 7/1997 | Rice .................. A61K 8/25 423/335 |
| 5,709,896 A | 1/1998 | Hartigan et al. |
| 5,711,985 A | 1/1998 | Guerrero et al. |

(Continued)

FOREIGN PATENT DOCUMENTS

| | | |
|---|---|---|
| AU | 2012202679 B2 | 3/2014 |
| CN | 2072973 U | 3/1991 |

(Continued)

OTHER PUBLICATIONS

Dowex Ion Exchange Resins. 2002. 12 pp.*

(Continued)

*Primary Examiner* — Nikki H. Dees

(74) *Attorney, Agent, or Firm* — Wilson, Sonsini, Goodrich & Rosati

(57) ABSTRACT

Provided herein are compositions with enhanced sweetness or reduced caloric content per weight when compared to the sweetener carbohydrate or sweetener polyol component thereof, and methods for the preparation thereof.

13 Claims, No Drawings

(56) References Cited

U.S. PATENT DOCUMENTS

| | | | |
|---|---|---|---|
| 6,123,926 A | 9/2000 | Parikh et al. | |
| 6,248,378 B1 | 6/2001 | Ganan-Calvo | |
| 6,251,464 B1 | 6/2001 | Felisaz et al. | |
| 6,428,827 B1 | 8/2002 | Song et al. | |
| 6,461,658 B1 | 10/2002 | Merkel et al. | |
| 6,548,264 B1 | 4/2003 | Tan et al. | |
| 6,652,611 B1* | 11/2003 | Huang | A61K 8/24 106/35 |
| 6,673,383 B2 | 1/2004 | Cain et al. | |
| 6,703,057 B2 | 3/2004 | Duffett | |
| 6,777,397 B2 | 8/2004 | Zehner et al. | |
| 7,118,765 B2 | 10/2006 | Norman et al. | |
| 7,122,215 B2 | 10/2006 | Ludwig et al. | |
| 7,163,708 B2 | 1/2007 | Dalziel et al. | |
| 7,258,885 B2 | 8/2007 | Seltzer et al. | |
| 7,267,835 B2 | 9/2007 | Kitazume et al. | |
| 7,282,217 B1 | 10/2007 | Grimshaw et al. | |
| 7,544,379 B2 | 6/2009 | Kawamura et al. | |
| 7,744,922 B2 | 6/2010 | Mane et al. | |
| 7,754,239 B2 | 7/2010 | Mane et al. | |
| 7,763,570 B1 | 7/2010 | Rayborn, Sr. et al. | |
| 7,815,936 B2 | 10/2010 | Hasenzahl et al. | |
| 7,838,033 B2 | 11/2010 | Tanaka et al. | |
| 7,838,055 B2 | 11/2010 | Eroma et al. | |
| 7,842,324 B2 | 11/2010 | Tachdjian et al. | |
| 7,851,005 B2 | 12/2010 | Hargreaves et al. | |
| 7,851,006 B2 | 12/2010 | Bingley et al. | |
| 7,879,376 B2 | 2/2011 | Boghani et al. | |
| 7,955,630 B2 | 6/2011 | Boghani et al. | |
| 7,972,995 B2 | 7/2011 | Rayborn, Sr. et al. | |
| 8,119,173 B2 | 2/2012 | Cheng et al. | |
| 8,192,775 B2 | 6/2012 | Eroma et al. | |
| 8,216,981 B2 | 7/2012 | Rayborn, Sr. et al. | |
| 8,349,361 B2 | 1/2013 | Tanaka et al. | |
| 8,545,889 B2 | 10/2013 | Norman et al. | |
| 8,617,588 B2 | 12/2013 | Tillotson et al. | |
| 8,647,668 B2 | 2/2014 | Tanaka et al. | |
| 8,663,682 B2 | 3/2014 | Chenevier et al. | |
| 8,673,825 B2 | 3/2014 | Rayborn, Sr. et al. | |
| 8,697,167 B2 | 4/2014 | Stouffs et al. | |
| 8,911,806 B2 | 12/2014 | Baniel | |
| 8,962,058 B2 | 2/2015 | Prakash et al. | |
| 9,023,418 B2 | 5/2015 | Baniel | |
| 9,028,906 B2 | 5/2015 | Baniel | |
| 9,144,251 B2 | 9/2015 | Prakash et al. | |
| 9,271,942 B2 | 3/2016 | Ramtoola | |
| 9,358,212 B2 | 6/2016 | Tillotson et al. | |
| 9,446,055 B2 | 9/2016 | Fujiwara et al. | |
| 9,668,504 B2 | 6/2017 | Baniel et al. | |
| 2001/0004869 A1 | 6/2001 | Cantiani et al. | |
| 2001/0055572 A1* | 12/2001 | Thomas | A61K 8/25 424/49 |
| 2003/0014014 A1 | 1/2003 | Nitzan | |
| 2003/0039617 A1* | 2/2003 | White, Jr. | A61Q 11/00 424/49 |
| 2003/0129227 A1 | 7/2003 | Yamaguchi | |
| 2004/0068224 A1 | 4/2004 | Couvillon et al. | |
| 2004/0161498 A1 | 8/2004 | Ripoll et al. | |
| 2005/0130240 A1 | 6/2005 | Lin et al. | |
| 2005/0244568 A1 | 11/2005 | Gokhan | |
| 2006/0024335 A1 | 2/2006 | Roger | |
| 2006/0073255 A1 | 4/2006 | Catani et al. | |
| 2006/0102455 A1 | 5/2006 | Chiang et al. | |
| 2007/0003680 A1 | 1/2007 | Tachdjian et al. | |
| 2007/0116827 A1 | 5/2007 | Prakash et al. | |
| 2007/0116832 A1 | 5/2007 | Prakash et al. | |
| 2008/0044521 A1 | 2/2008 | Eddies et al. | |
| 2008/0193531 A1 | 8/2008 | Hermelin et al. | |
| 2008/0213452 A1 | 9/2008 | Miles et al. | |
| 2008/0292765 A1 | 11/2008 | Prakash et al. | |
| 2008/0311398 A1* | 12/2008 | Bauer | A61K 8/25 428/402 |
| 2009/0053378 A1 | 2/2009 | Prakash et al. | |
| 2009/0297670 A1 | 12/2009 | Baniel | |
| 2010/0129516 A1 | 5/2010 | Siegel | |
| 2011/0027355 A1 | 2/2011 | Lefevre et al. | |
| 2011/0027444 A1 | 2/2011 | Gelov | |
| 2011/0052755 A1 | 3/2011 | Fiorenza et al. | |
| 2011/0059218 A1 | 3/2011 | Corliss et al. | |
| 2011/0064861 A1 | 3/2011 | Shimono et al. | |
| 2012/0088025 A1 | 4/2012 | Baniel et al. | |
| 2012/0207890 A1 | 8/2012 | Johal et al. | |
| 2013/0236604 A1 | 9/2013 | De Baets | |
| 2013/0273165 A1 | 10/2013 | Buchner | |
| 2014/0010939 A1 | 1/2014 | Krohn et al. | |
| 2014/0271747 A1 | 9/2014 | Woodyer et al. | |
| 2015/0150292 A1 | 6/2015 | Baniel | |
| 2015/0189904 A1 | 7/2015 | Prakash et al. | |
| 2015/0275319 A1 | 10/2015 | Baniel | |
| 2015/0289550 A1 | 10/2015 | Baniel et al. | |
| 2016/0045518 A1 | 2/2016 | Dohil et al. | |
| 2016/0242439 A1 | 8/2016 | Baniel et al. | |
| 2016/0331012 A1 | 11/2016 | Baniel et al. | |
| 2017/0215461 A1 | 8/2017 | Baniel et al. | |

FOREIGN PATENT DOCUMENTS

| | | |
|---|---|---|
| CN | 103504256 A | 1/2014 |
| EP | 0427541 A2 | 5/1991 |
| EP | 1447074 A2 | 8/2004 |
| EP | 1901617 B1 | 10/2009 |
| FR | 2808657 B1 | 6/2003 |
| GB | 721605 A | 1/1955 |
| GB | 2025227 A | 1/1980 |
| HK | 1158629 A1 | 10/2015 |
| IL | 180687 A | 4/2011 |
| JP | H04364122 A | 12/1992 |
| JP | 2001352936 A | 12/2001 |
| NZ | 556774 A | 2/2011 |
| WO | WO-9012117 A2 | 10/1990 |
| WO | WO-9414330 A1 | 7/1994 |
| WO | WO-9416576 A1 | 8/1994 |
| WO | WO-9920127 A1 | 4/1999 |
| WO | WO-0113740 A1 | 3/2001 |
| WO | WO-02051391 A2 | 7/2002 |
| WO | WO-02096213 A1 | 12/2002 |
| WO | WO-03045166 A1 | 6/2003 |
| WO | WO-2004005227 A1 | 1/2004 |
| WO | WO-2004066974 A1 | 8/2004 |
| WO | WO-2004089113 A1 | 10/2004 |
| WO | WO-2004098555 A1 | 11/2004 |
| WO | WO-2005037254 A1 | 4/2005 |
| WO | WO-2005037849 A1 | 4/2005 |
| WO | WO-2005084457 A1 | 9/2005 |
| WO | WO-2006012763 A1 | 2/2006 |
| WO | WO-2006015880 A1 | 2/2006 |
| WO | WO-2006062089 A1 | 6/2006 |
| WO | WO-2006072921 A2 | 7/2006 |
| WO | WO-2007007310 A1 | 1/2007 |
| WO | WO-2007061757 A1 | 5/2007 |
| WO | WO-2007061810 A2 | 5/2007 |
| WO | WO-2007061858 A1 | 5/2007 |
| WO | WO-2007061900 A1 | 5/2007 |
| WO | WO-2007061912 A2 | 5/2007 |
| WO | WO-2007081442 A2 | 7/2007 |
| WO | WO-2008042417 A1 | 4/2008 |
| WO | WO-2009006208 A2 | 1/2009 |
| WO | WO-2009087215 A2 | 7/2009 |
| WO | WO-2009151072 A1 | 12/2009 |
| WO | WO-2010025158 A1 | 3/2010 |
| WO | WO-2011019045 A1 | 2/2011 |
| WO | WO-2013045318 A1 | 4/2013 |
| WO | WO-2013082019 A1 | 6/2013 |
| WO | WO-2014080394 A1 | 5/2014 |
| WO | WO-2015015210 A1 | 2/2015 |
| WO | WO-2015150915 A2 | 10/2015 |
| WO | WO-2015159156 A2 | 10/2015 |
| WO | WO-2015159156 A3 | 2/2016 |
| WO | WO-2015150915 A3 | 3/2016 |
| WO | WO-2017037531 A2 | 3/2017 |
| WO | WO-2017037531 A3 | 4/2017 |
| WO | WO-2017072569 A1 | 5/2017 |

(56) References Cited

FOREIGN PATENT DOCUMENTS

OTHER PUBLICATIONS

International Search Report and Written Opinion dated Feb. 9, 2017 for PCT Application No. PCT/IB2016/01322.
International Search Report and Written Opinion dated Feb. 16, 2017 for PCT Application No. PCT/IB2016/01284.
Notice of allowance dated Mar. 22, 2017 for U.S. Appl. No. 14/528,750.
Office action dated Nov. 18, 2016 for U.S. Appl. No. 14/528,750.
Office action dated Dec. 29, 2016 for U.S. Appl. No. 14/629,272.
Al-Ghouti, et al. New adsorbents based on microemulsion modified diatomite and activated carbon for removing organic and inorganic pollutants from waste lubricants. Chemical Engineering Journal vol. 173, Issue 1 Sep. 2011, 115-128.
Co-pending U.S. Appl. No. 14/440,975, filed May 6, 2015.
Co-pending U.S. Appl. No. 14/629,272, filed Feb. 23, 2015.
Co-pending U.S. Appl. No. 14/677,715, filed Apr. 2, 2015.
Co-pending U.S. Appl. No. 15/045,145, filed Feb. 16, 2016.
Fennema, Food Chemistry Third Edition 1996, Marcel Drekker Publication, Pertinent p. 193.
Graneinetti Laboratory (undated) http://www.grandinetti.org/Teaching/Chem121/Lectures/VSEPR.
Handbuch Subungsmittel: Eigenschaften and Anwendung. pp. 162-165. G.W. von Rymon Lipinski and H. Hamburg, Germany (1990). ISBN: 3-925673-77-6 (in German).
International search report and written opinion dated Jan. 7, 2016 for PCT Application No. PCT-IB15-00773.
International search report and written opinion dated Apr. 4, 2014 for PCT Application No. IL2013/050851.
International search report and written opinion dated Jul. 20, 2006 for PCT Application No. IL2006/00573.
International search report and written opinion dated Nov. 30, 2015 for PCT/IB2015/001153.
Kelly, et al. Phase Equilibria in the System Sucrose-Glucose-Fructose. J. appl. Chem. May 4, 1967. 17.5: 125-126.
Lionnet, et al. Aspects of the Effects of Silica During Cane Sugar Processing. Proc S Afr Sug Technol Ass. vol. 78. 2004, 55-64.
Madho, et al. Silica in low grade refinery sugar Proc S Afr Sug Technol Ass. vol. 84. 2011, 516-527.
Middle School Chemistry (undated) http://www.middleschoolchemistry.com/multimedia/chapter4/lesson6.
Notice of Allowance dated Jan. 2, 2015 for U.S. Appl. No. 13/250,088.
Notice of allowance dated Feb. 13, 2015 for U.S. Appl. No. 14/511,046.
Notice of allowance dated Oct. 6, 2014 for U.S. Appl. No. 11/995,464.
Office action dated Jan. 7, 2013 for U.S. Appl. No. 13/250,088.
Office action dated Jan. 10, 2013 for U.S. Appl. No. 11/995,464.
Office action dated Jan. 10, 2014 for U.S. Appl. No. 11/995,464.
Office action dated Jan. 22, 2016 for U.S. Appl. No. 14/629,272.
Office action dated Mar. 28, 2016 for U.S. Appl. No. 14/440,975.
Office action dated Apr. 18, 2012 for U.S. Appl. No. 11/995,464.
Office action dated May 30, 2013 for U.S. Appl. No. 13/250,088.
Office action dated Jul. 30, 2014 for U.S. Appl. No. 13/250,088.
Office action dated Aug. 15, 2011 for U.S. Appl. No. 11/995,464.
Office action dated Sep. 10, 2014 for U.S. Appl. No. 13/250,088.
Pending claims dated May 15, 2014 for U.S. Appl. No. 13/250,088.
Pending claims dated Aug. 28, 2014 for U.S. Appl. No. 13/250,088.
Smith, Jim; Hong-Shum, Lily (2003). Food Additives Data Book. (pp. 704-707). Blackwell Publishing. Online version available at: http://www.knovel.com/web/portal/browse/display?_EXT_KNOVEL_DISPLAY_bookid=1381&VerticalID=0.
The surface chemistry of amorphous silica. Zhuravlev model L.T. Zhuravlev Institute of Physical Chemistry, Russian Academy of Sciences, Leninsky Prospect 31, Moscow 117915, Russia Feb. 2000 Elsevier, 38 pages.
U.S. Appl. No. 14/528,750 Office Action dated May 9, 2016.
U.S. Appl. No. 14/629,272 Office Action dated May 25, 2016.
U.S. Appl. No. 15/045,145 Office Action dated Aug. 15, 2016.
Co-pending U.S. Appl. No. 15/489,696, filed Apr. 17, 2017.
"International search report with written opinion dated Dec. 12, 2016 for PCT/IB2016/00818".
"Tamura M, et al. An enhancing effect on the saltiness of sodium chloride of added amino acids and their esters. Agricultural and Biological Chemistry. 1989, vol. 53, No. 6, pp. 1625-1633".
Bergna, Horacio E, Ed. The Colloidal Chemistry of Silica, ACS Publications, p. 21-30, 341-353, 1994.
European search report and search opinion dated Oct. 27, 2017 for European Patent Application No. 15780074.9.
Hafiz, et al. Synthesis of quality silica gel; Optimization of parameters. Journal of Faculty of Engineering & Technology, 2009, 14 pages.
Kinrade, et al. Aqueous hypervalent silicon complexes with aliphatic sugar acids. J. Chem. Soc., Dalton Trans., 2001,0, 961-963.
Kinrade, et al. Silicon-29 NMR evidence of alkoxy substituted aqueous silicate anions. J. Chem. Soc., Dalton Trans., 1999, 3149-3150.
Kinrade, et al. Stable five- and six-coordinated silicate anions in aqueous solution. Science. Sep. 3, 1999;285(5433):1542-5.
Martin, K.R. The Chemistry of Silica and Its Potential Health Benefits. The Journal of Nutrition, Health & Aging; Paris vol. 11(2), (Mar./Apr. 2007): 94-7.
Office action dated Sep. 18, 2017 for U.S. Appl. No. 15/487,274.
Rombauer, I. S., Rombauer Becker, M., Becker, E. 1997. Joy of Cooking. Scribner: New York. p. 1010.
Storer, Ian. Hypervalent Silicon: Bonding, Properties and Synthetic Utility, MacMillan Group Meeting, Jul. 20, 2005.
Co-pending U.S. Appl. No. 15/756,040, filed Feb. 27, 2018.
Co-pending U.S. Appl. No. 15/756,042, filed Feb. 27, 2018.
Narducci, Olga. Particle Engineering via Sonocrystallization: The Aqueous Adipic Acid System. University College of London: Department of Chemical Engineering. p. 65 of Ph.D. Thesis. Oct. 2012. 2 pages.
U.S. Appl. No. 14/629,272 Notice of Allowance dated Sep. 25, 2018.
U.S. Appl. No. 15/487,274 Notice of Allowance dated Nov. 9, 2018.
U.S. Appl. No. 15/489,696 Notice of Allowance dated Oct. 4, 2018.
U.S. Appl. No. 14/629,272 Notice of Allowance dated Oct. 17, 2018.
U.S. Appl. No. 14/629,272 Notice of Allowance dated Oct. 5, 2018.
U.S. Appl. No. 15/489,696 Notice of Allowance dated Dec. 12, 2018.

\* cited by examiner

SWEETENER COMPOSITIONS AND FOODS, BEVERAGES, AND CONSUMABLE PRODUCTS MADE THEREOF

CROSS-REFERENCE

This application is a continuation application of International Application No. PCT/IB2015/001153, filed Apr. 3, 2015, which claims the benefit of U.S. Provisional Application No. 61/975,683, filed Apr. 4, 2014; U.S. Provisional Application No. 62/042,154, filed Aug. 26, 2014; U.S. Provisional Application No. 62/074,518, filed Nov. 3, 2014; and U.S. Provisional Application No. 62/140,299, filed Mar. 30, 2015; each of which is hereby incorporated by reference in its entirety.

FIELD OF THE INVENTION

The present disclosure relates to sweetener compositions. More particularly, the present invention relates to carbohydrate sweetener compositions and polyol sweetener compositions having enhanced sweetness and reduced caloric content as compared to that of the carbohydrate component or polyol component thereof, and to methods for the preparation thereof.

BACKGROUND OF THE INVENTION

Certain carbohydrates and polyols are commonly used as sweeteners. Sucrose, glucose, and other sweet mono-saccharides, di-saccharides, and oligosaccharides are fully metabolized when consumed in food. The sweetness of these natural sweeteners correlates with their calories in a fixed proportion. Excess sugar intake can pose several health problems. Artificial sweeteners have been used to reduce dietary sugar content, but they are not ideal sugar substitutes due to their after taste, absence of energy provided by sugars, and other health concerns. Sweetener polyols can offer a reduced calorie load and varying sweetness as compared to sweetener carbohydrates, but the cost of some sweetener polyols can be high. In such cases, a method to increase the sweetness of sweetener carbohydrates or sweetener polyols or to reduce the amount of sweetener carbohydrates or sweetener polyols while achieving equivalent sweetness is desired. Another promising strategy focuses on allosteric modulation of the sweet taste receptor by sweet taste enhancers. These artificially synthesized molecules do not taste sweet but can significantly modulate the perception of sweetness for sucrose and other sweeteners; however, they can be limited in strength and selectivity and have so far been tested on limited products. The present disclosure provides for the manipulation of the proportion between sweetener amount and calories so that a desired sweetness may correlate with lower calorie values while retaining a similar sensory profile to the sweetener. This effect is achieved through the presentation of the carbohydrate sweetener or polyol sweetener in the form of a composition belonging to a class of compositions described below. The perception of sweetness of a sweetener carbohydrate or sweetener polyol is retained while reducing the caloric value thereof by virtue of it being provided in a composition as described hereinafter.

SUMMARY OF THE INVENTION

Provided herein is a method of producing a sweetener composition, comprising mixing one or more sweetener carbohydrates and/or sweetener polyols with a carrier compound precursor and a catalyst to form a sweetener composition; wherein the sweetener composition comprises one or more sweetener carbohydrates and/or sweetener polyols and a carrier compound; wherein the sweetener composition has enhanced sweetness compared to a control composition; and wherein the control composition consists of the same contents by identity and quantity as the one or more sweetener carbohydrates and/or sweetener polyols. In some cases, the method further comprises drying the sweetener composition. In some cases, the method further comprises sonicating the sweetener composition. In some cases, the method further comprises passing the sweetener composition through a sieve. In some cases, the method further comprises passing the sweetener composition through a sieve or sieving tower to remove particles of particular sizes and to form a selectively sieved sweetener composition. In some cases, the method further comprises filtering the sweetener composition. In some cases, the method further comprises mechanical grinding of the sweetener composition by mortar and pestle or mechanical grinder. In some cases, the method may comprise forming a carrier compound in the presence of one or more sweetener carbohydrates and/or sweetener polyols to form a sweetener composition. In some cases, the carrier compound is formed in situ in the presence of one or more sweetener carbohydrates and/or sweetener polyols. In some cases, the one or more sweetener carbohydrates are selected from the group consisting of sucrose, glucose, fructose, maltose, lactose, high fructose corn syrup, high maltose corn syrup, and a combination thereof. In some cases, the one or more sweetener carbohydrates are sucrose, glucose, fructose, or a combination thereof. In some cases, the sweetener carbohydrate is high fructose corn syrup. In some cases, the one or more sweetener polyols are selected from the group consisting of xylitol, maltitol, erythritol, sorbitol, threitol, arabitol, hydrogenated starch hydrolysates, isomalt, lactitol, mannitol, galactitol (dulcitol), and a combination thereof. In some cases, the carrier compound is silica. In some cases, the carrier compound precursor is a silicate. In some cases, the silicate is sodium silicate, potassium silicate, calcium silicate, aluminum silicate, tetramethylammonium silicate, sodium metasilicate, sodium metasilicate hydrate, calcium metasilicate, or a combination thereof. In some cases, the silicate is sodium silicate. In some cases, the carrier compound precursor is silicic acid. In some cases, the catalyst is an acid, ion exchange resin, ion exchange polymer, or a combination thereof. In some cases, the acid is a weak acid, strong acid, or a combination thereof. In some cases, the acid is acetic acid, aconitic acid, adipic acid, alginic acid, ascorbic acid, benzoic acid, caprylic acid, carbonic acid, citric acid, fumaric acid, hydrochloric acid, lactic acid, linoleic acid, malic acid, phosphoric acid, propionic acid, sorbic acid, stearic acid, succinic acid, sulfuric acid, tannic acid, tartaric acid, vinegar, or a combination thereof. In some cases, the acid is citric acid, phosphoric acid, or a combination thereof. In some cases, the catalyst is an ion exchange resin, ion exchange polymer, or a combination thereof. In some cases, the ion exchange resin is Dowex 88(H) or Purolite SST C60H. In some cases, the sweetness is enhanced by at least 10, 20, 30, 40, or 50%.

Further provided herein is a method of producing silica, comprising mixing one or more sweetener carbohydrates and/or sweetener polyols with a carrier compound precursor and a catalyst to form silica. In some cases, the one or more sweetener carbohydrates are selected from the group consisting of sucrose, glucose, fructose, maltose, lactose, high fructose corn syrup, high maltose corn syrup, and a combination thereof. In some cases, the one or more sweetener carbohydrates are sucrose, glucose, fructose, or a combination thereof. In some cases, the sweetener carbohydrate is high fructose corn syrup. In some cases, the one or more sweetener polyols are selected from the group consisting of xylitol, maltitol, erythritol, sorbitol, threitol, arabitol, hydrogenated starch hydrolysates, isomalt, lactitol, mannitol, galactitol (dulcitol), and a combination thereof. In some cases, the carrier compound precursor is a silicate. In some cases, the silicate is sodium silicate, potassium silicate, calcium silicate, aluminum silicate, tetramethylammonium silicate, sodium metasilicate, sodium metasilicate hydrate, calcium metasilicate, or a combination thereof. In some cases, the silicate is sodium silicate. In some cases, the carrier compound precursor is silicic acid. In some cases, the catalyst is an acid, ion exchange resin, ion exchange polymer, or a combination thereof. In some cases, the acid is a weak acid, strong acid, or a combination thereof. In some cases, the acid is acetic acid, aconitic acid, adipic acid, alginic acid, ascorbic acid, benzoic acid, caprylic acid, carbonic acid, citric acid, fumaric acid, hydrochloric acid, lactic acid, linoleic acid, malic acid, phosphoric acid, propionic acid, sorbic acid, stearic acid, succinic acid, sulfuric acid, tannic acid, tartaric acid, vinegar, or a combination thereof. In some cases, the acid is citric acid, phosphoric acid, or a combination thereof. In some cases, the catalyst is an ion exchange resin, ion exchange polymer, or a combination thereof. In some cases, the ion exchange resin is Dowex 88(H) or Purolite SST C60H.

Also provided herein is a sweetener composition comprising one or more sweetener carbohydrates and/or sweetener polyols and 0.05-4% carrier compound weight/weight relative to a sum of total sweetener carbohydrate and sweetener polyol; wherein the sweetener composition has enhanced sweetness compared to a control composition; and wherein the control composition consists of the same contents by identity and quantity as the one or more sweetener carbohydrates and/or sweetener polyols. In some cases, the composition may comprise about 0.05-2% carrier compound weight/weight relative to a sum of total sweetener carbohydrate and sweetener polyol. In some cases, the composition may comprise about 0.1-0.6% carrier compound weight/weight relative to a sum of total sweetener carbohydrate and sweetener polyol. In some cases, the composition may comprise about 0.3-0.4% carrier compound weight/weight relative to a sum of total sweetener carbohydrate and sweetener polyol. In some cases, the one or more sweetener carbohydrates are selected from the group consisting of sucrose, glucose, fructose, maltose, lactose, high fructose corn syrup, high maltose corn syrup, and a combination thereof. In some cases, the one or more sweetener polyols are selected from the group consisting of xylitol, maltitol, erythritol, sorbitol, threitol, arabitol, hydrogenated starch hydrolysates, isomalt, lactitol, mannitol, galactitol (dulcitol), and a combination thereof. In some cases, the carrier compound is silica. In some cases, the sweetener composition is an isolated sweetener composition. In some cases, a sweetener composition described herein reduces the perceived bitterness of a consumable product, such as a food, beverage, or other non-food, non-beverage consumable product.

Further provided herein is a formulation comprising a sweetener composition. In some cases, the formulation is a syrup (i.e., a sweetener composition formulated as a syrup). A formulation can include water. A formulation can include a food additive. A formulation can include an artificial sweetener, a natural sugar substitute, or a combination thereof. An artificial sweetener can be one that is selected from the group consisting of: acesulfame potassium, advantame, alitame, aspartame, sodium cyclamate, dulcin, glucin, neohesperidin dihydrochalcone, neotame, P-4000, saccharin, aspartame-acesulfame salt, and sucralose. A natural sugar substitute can be one that is selected from the group consisting of: brazzein, curculin, glycyrrhizin, glycerol, inulin, mogroside, mabinlin, malto-oligosaccharide, mannitol, miraculin, monatin, monellin, osladin, pentadin, stevia, tagatose, and thaumatin. Any of the sweetener compositions, formulations, or consumable products described herein preferably have a reduced perceived bitterness as compared to the same product made using an artificial sweetener and/or a natural sugar substitute instead of a sweetener composition or made without a sweetener composition as described herein.

The sweetener compositions and formulations described herein can be used to make consumable products. Consumable products include food products, beverage products, pharmaceutical products, and hygiene products, as non-limiting examples. Food products include, but are not limited to, confectionary, chocolate, jam, ice cream, soup, whipped cream, baked goods, condiments, sauces, dairy products, and dressings. Beverage products include, but are not limited to, soft drink, flavored water, juice, sports drink, energy drink, alcoholic beverage, liqueur, carbonated beverage, caffeinated beverage, coffee, cocoa, tea, and dairy drinks. Pharmaceutical products include, but are not limited to, cough syrups, capsules, and tablets. Hygiene products include, but are not limited to, tooth paste and mouth wash. Other miscellaneous consumable products include, but are not limited to, chewing gum and spices.

In some cases, a consumable product may contain up to 0.1, 0.5, 1.0, 1.1, 1.2, 1.3, 1.4, 1.5, 1.6, 1.7, 1.8, 1.9, or 2.0% silica on a weight/weight basis. In some cases, the consumable product is less bitter than a control product, wherein the control product is identical to the consumable product and has the same sweetener carbohydrate and/or sweetener polyol but not formulated as a sweetener composition (i.e., with the carrier).

Additionally provided herein are methods to make a consumable product. Such methods comprise substituting a portion of a sweetener ingredient in a consumable product with a sweetener composition described herein. Additionally or alternatively, a sweetener composition can be added to the process of making the consumable product.

The novel features of the invention are set forth with particularity in the appended claims. A better understanding of the features and advantages of the present invention will be obtained by reference to the following detailed description that sets forth illustrative embodiments, in which the principles of the invention are utilized.

DETAILED DESCRIPTION OF THE INVENTION

Introduction

The present disclosure relates to sweetener compositions that can be used alone, formulated into sweetener composition formulations, or added to or further processed into a consumable product. The sweetener compositions herein comprise one or more sweetener carbohydrates and/or sweetener polyols and a carrier compound. The sweetener compositions herein may be sweeter in taste than a similar control composition (e.g., a composition comprising the same contents by identity and quantity as the one or more carbohydrates and/or polyols but without the carrier compound).

Definitions

As used herein, the term "sweetener carbohydrate" refers to a consumable carbohydrate, which produces a sweet taste when consumed alone. A sweetener carbohydrate may be a monosaccharide or disaccharide. A sweetener carbohydrate may be a naturally-occurring carbohydrate. For example, it may be an isolated, purified sweetener. A sweetener carbohydrate may be a non-naturally occurring or synthetically-produced carbohydrate. Non-limiting examples of a sweetener carbohydrate include sucrose, glucose, fructose, maltose, lactose, high fructose corn syrup, and high maltose corn syrup. A sweetener carbohydrate may be sucrose, glucose, fructose, maltose, lactose, or a combination thereof. A sweetener carbohydrate may be sucrose, glucose, fructose, or a combination thereof. A sweetener carbohydrate may be sucrose. A sweetener carbohydrate may be glucose. A sweetener carbohydrate may be fructose. A sweetener carbohydrate may be high fructose corn syrup, high maltose corn syrup, or a combination thereof. A sweetener carbohydrate may be high fructose corn syrup. A sweetener carbohydrate may be high maltose corn syrup.

As used herein, the term "sweetener polyol" refers to a consumable polyol, which produces a sweet taste when consumed alone. Non-limiting examples of sweetener polyols include xylitol, maltitol, erythritol, sorbitol, threitol, arabitol, hydrogenated starch hydrolysates, isomalt, lactitol, mannitol, and galactitol (dulcitol). The polyol may be a sugar alcohol. A sugar alcohol may be produced from a corresponding parent carbohydrate by any known method of reduction (via a chemical or biological transformation) of a carboxylic acid or aldehyde to an alcohol. A sweetener polyol may be created synthetically from a parent carbohydrate. Alternatively or in combination, a sweetener polyol may be bio-derived or obtained from a biological source.

As used herein, the term "sweetener" or "sweetener ingredient" refers to a consumable product, which produces a sweet taste when consumed alone. Some non-limiting examples of a sweetener ingredient include a sweetener carbohydrate, sweetener polyol, artificial sweetener, and natural sugar substitute.

As used herein, the term "carrier compound" refers to a solid, food-grade material, which may be coated with a sweetener. A carrier compound through its large and active surface and structure may form hydrogen bonds or van der Waals bonds with a sweetener carbohydrate and/or sweetener polyol. As such, the carbohydrate and/or polyol can maintain its chemical integrity. For instance, the interaction between the carrier compound and the carbohydrate and/or polyol does not need to involve covalent bonds. The carrier compound may associate with the sweetener carbohydrate and/or sweetener polyol to provide characteristics different than a control composition, for instance enhanced sweetness, reduced bitterness, or reduced rate of dissolution. A carrier compound may be a solid composition lacking a distinctive taste. A carrier compound may be tasteless, flavorless, or odorless. Digestion of a carrier compound by a human may produce a low amount of usable calories. A carrier compound may be non-caloric. A carrier compound may at least partially dissolve in a solvent (e.g., water). A carrier compound optionally meets test requirements as described in the Food Chemicals Codex (FCC), the European Directive, or Japan's Specifications and Standards for Food Additives. A carrier compound may be formed from a carrier compound precursor. A carrier compound may be formed from a reaction between a carrier compound precursor and a catalyst. A carrier compound may be formed, precipitated, or dispersed in the presence of one or more sweetener carbohydrates and/or sweetener polyols.

Non-limiting examples of a carrier compound include silica and silicon dioxide. A carrier compound may comprise silica or silicon dioxide ($SiO_2$). The carrier compound may comprise silica or silicon dioxide. The carrier compound may be silica or silicon dioxide. The carrier compound may be silica. Non-limiting examples of silica include precipitated silica, porous silica, amorphous silica, colloidal silica, dispersed silica, and silica gel. In some cases when the carrier compound is silica, the sweetness of a sweetener composition can have a ratio of silica to sweetener carbohydrate and/or sweetener polyol that gives a maximum sweetness. Increasing the amount of silica relative to sweetener carbohydrate and/or sweetener polyol beyond the maximum point can decrease the sweetness of the composition. In some cases, wherein the amount of silica is higher than the maximum sweetness amount, a grainy, sandy, or chalky characteristic can enter the taste profile. In some cases, when the amount of silica is less than the maximum sweetness amount, the composition does not fully benefit from the sweetness enhancement effect of the silica.

A carrier compound may have a high specific surface area. In some cases, a carrier compound may have a specific surface area of at least 20, 30, 40, 50, 60, 70, 80, 90, 100, 110, 120, 130, 140, 150, 160, 170, 180, 190, 200, 210, 220, 230, 240, 250, 260, 270, 280, 290, or 300 $m^2/g$. In some cases, a carrier compound may have a specific surface area of up to 20, 30, 40, 50, 60, 70, 80, 90, 100, 110, 120, 130, 140, 150, 160, 170, 180, 190, 200, 210, 220, 230, 240, 250, 260, 270, 280, 290, or 300 $m^2/g$. In some cases, a carrier compound may have a specific surface area of about 20, 30, 40, 50, 60, 70, 80, 90, 100, 110, 120, 130, 140, 150, 160, 170, 180, 190, 200, 210, 220, 230, 240, 250, 260, 270, 280, 290, or 300 $m^2/g$.

As used herein, the term "carrier compound precursor" refers to a material, which may undergo a chemical reaction to form a carrier compound. The carrier compound precursor may be a silicate. Non-limiting examples of silicate include sodium silicate, potassium silicate, calcium silicate, aluminum silicate, tetramethylammonium silicate, sodium metasilicate, sodium metasilicate hydrate, and calcium metasilicate. In some cases, the silicate is sodium silicate. In some cases, the carrier compound precursor may be silicic acid. A carrier compound precursor may be a combination of two or more distinct carrier compound precursors. In some cases, a carrier compound precursor comprises a carrier compound precursor counterion (e.g., sodium ion in sodium silicate).

As used herein, the term "catalyst" refers to a reagent, which may be undergo a chemical reaction with a carrier compound precursor to form a carrier compound. The catalyst may be food permitted. The catalyst may be generally recognized as safe. The catalyst may be one or more acids, bases, ion exchange resins, ion exchange polymers, or a combination thereof. The catalyst may be one or more acids, ion exchange resins, or a combination thereof. The catalyst may be an acid. The catalyst may be an ion exchange resin or ion exchange polymer. The acid may be a weak acid, strong acid, or a combination thereof. Non-limiting examples of an acid include acetic acid, aconitic acid, adipic acid, alginic acid, ascorbic acid, benzoic acid, caprylic acid, carbonic acid, citric acid, fumaric acid, hydrochloric acid, lactic acid, linoleic acid, malic acid, phosphoric acid, propionic acid, sorbic acid, stearic acid, succinic acid, sulfuric acid, tannic acid, tartaric acid, and vinegar. The ion exchange resin may be a cation exchange resin or anion exchange resin. The ion exchange resin may be a strong acid resin or a weak acid resin. The ion exchange resin may be Dowex 88(H) or Purolite SST C60H. A catalyst may be a combination of two or more distinct catalysts. In some cases, two or more catalysts can be used in series or in parallel. In some cases, the catalyst is regenerated. In some cases, the catalyst is not regenerated. In some cases, the catalyst does not turn over. In some cases, an unregenerated or nonregenerated catalyst is a conjugate acid or conjugate base.

As used herein, the term "solvent" refers to a liquid, which may be mixed with or used to dissolve a sweetener composition or one or more components of a sweetener composition. Non-limiting examples of a solvent include water, ethanol, and isopropanol. The solvent can be potable. The solvent can be water. Non-limiting examples of water include purified water, distilled water, double distilled water, deionized water, distilled deionized water, drinking water, well water, tap water, spring water, bottled water, carbonated water, mineral water, flavored water, or a combination thereof. A solvent may be a combination of two or more distinct solvents.

As used herein, the term "control composition" refers to a composition, to which a sweetener composition is compared. In some cases, a control composition comprises the one or more sweetener carbohydrates and/or sweetener polyols but not the carrier compound of the sweetener composition to which it is compared. In some cases, a control composition is formulated similarly to the sweetener composition. In some cases, a control composition is formulated identically to the sweetener composition. The control composition may comprise the same contents by identity and quantity as the one or more sweetener carbohydrates and/or sweetener polyols of a sweetener composition. In some cases, the one or more sweetener carbohydrates and/or sweetener polyols are in free, unassociated form. The control composition may consist of the same contents by identity and quantity as the one or more sweetener carbohydrates and/or sweetener polyols of a sweetener composition. In other cases, the control composition may consist of the same contents by identity and quantity as the sweetener composition but without the carrier compound. The control composition may consist of the same contents by identity and quantity as the sweetener composition but without carrier compound, unreacted carrier compound precursor, unreacted catalyst, carrier compound precursor counterion, and/or unregenerated catalyst.

As used herein, the term "enhanced sweetness" or "higher perceived sweetness" refers to a stronger or higher sense of sweetness to a human. Sweetener compositions with enhanced sweetness taste sweeter than the control composition to which they are compared. A smaller amount (by weight or by volume) of a sweetener composition with enhanced sweetness may produce the same sense of sweetness as a larger amount (by weight or by volume) of a control composition that lacks enhanced sweetness. A sweetener composition with enhanced sweetness may produce a higher perceived sweetness and a lower caloric content than a control composition with a comparable amount (by weight) of the one or more sweetener carbohydrates and/or sweetener polyols in free, unassociated form. For example, 1.0 grams of a sweetener composition comprising about 0.01 grams of a carrier coated with about 0.99 grams of one or more sweetener carbohydrates and/or sweetener polyols may produce a higher perceived sweetness than a control composition that comprises about 0.99 grams of the one or more sweetener carbohydrates and/or sweetener polyols and does not comprise the carrier compound.

As used herein, the term "consumable product" refers to a product, which may be consumed (e.g., by eating, chewing, drinking, or swallowing). Consumable products include food products, beverage products, pharmaceutical products, and hygiene products, as non-limiting examples. Food products include, but are not limited to, confectionary, chocolate, jam, ice cream, soup, whipped cream, baked goods, condiments, sauces, dairy products, and dressings. Beverage products include, but are not limited to, soft drink, flavored water, juice, sports drink, energy drink, alcoholic beverage, liqueur, carbonated beverage, caffeinated beverage, coffee, cocoa, tea, and dairy drinks. Pharmaceutical products include, but are not limited to, cough syrups, capsules, and tablets. Hygiene products include, but are not limited to, tooth paste and mouth wash. Other miscellaneous consumable products include, but are not limited to, chewing gum and spices.

As used herein, the term "about" can be understood as within 10%, 9%, 8%, 7%, 6%, 5%, 4%, 3%, 2%, 1%, 0.5%, 0.1%, 0.05%, or 0.01% of the stated value.

In some cases, the term "portion" can be understood as about 0.01, 0.05, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 91, 92, 93, 94, 95, 96, 97, 98, 99, 99, 99.1, 99.2, 99.3, 99.4, 99.5, 99.6, 99.7, 99.8, 99.9, or 100% of the referenced value; at least 0.01, 0.05, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 91, 92, 93, 94, 95, 96, 97, 98, 99, 99, 99.1, 99.2, 99.3, 99.4, 99.5, 99.6, 99.7, 99.8, 99.9, or 100% of the referenced value; or up to 0.01, 0.05, 0.1, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 91, 92, 93, 94, 95, 96, 97, 98, 99, 99, 99.1, 99.2, 99.3, 99.4, 99.5, 99.6, 99.7, 99.8, 99.9, or 100% of the referenced value.

In some cases, the term "one or more" can be understood as about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100; at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100; or up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100.

Sweetener Compositions

A sweetener composition comprises one or more sweetener carbohydrates and/or sweetener polyols and a carrier compound. In some cases, a sweetener composition comprises one or more sweetener carbohydrates and a carrier compound. In some cases, a sweetener composition comprises one or more polyols and a carrier compound. In some cases, a sweetener composition does not contain a sweetener carbohydrate. In some cases, a sweetener composition does not contain a sweetener polyol. A sweetener composition can be purified or isolated. A sweetener composition is preferably substantially uniform or homogenous. A sweetener composition can be in the form of a solid (e.g., a powder) or a syrup. In some cases, a sweetener composition is dry and/or dehydrated. In some cases, a sweetener composition can be in a solvent (e.g., water).

The sweetener composition herein can have a defined ratio of amounts of the carrier compound and the one or more sweetener carbohydrates and/or sweetener polyols. Such a ratio of amounts can be determined by mass, weight, volume, mole, or a combination thereof. In some examples, a ratio of the carrier compound to a sum of total sweetener carbohydrate and sweetener polyol can be at least 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or 4.0%. In other examples, a ratio of the carrier compound to a sum of total sweetener carbohydrate and sweetener polyol can be up to 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or 4.0%. In other examples, a ratio of the carrier compound to a sum of total sweetener carbohydrate and sweetener polyol can be about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, or 4.0%. In other examples, a ratio of the carrier compound to a sum of total sweetener carbohydrate and sweetener polyol can be between about 0.01-4.0%, 0.01-3.0%, 0.01-2.0%, 0.01-1.0%, 0.05-4.0%, 0.05-3.0%, 0.05-2.0%, 0.05-1.0%, 0.1-1.0%, 0.1-0.9%, 0.1-0.8%, 0.1-0.7%, 0.1-0.6%, 0.1-0.5%, 0.1-0.4%, 0.2-0.6%, 0.2-0.5%, 0.2-0.4%, 0.3-0.4%, 1.0-2.0%, 1.0-3.0%, 1.0-4.0%, 2.0-4.0%, or 3.0-4.0%. A ratio of the carrier compound to a sum of total sweetener carbohydrate and sweetener polyol can be about 0.05-4%.

A sweetener composition may have enhanced sweetness compared to a control composition. Preferably, the control composition is the one or more sweetener carbohydrates and/or sweetener polyols but not the carrier compound of the sweetener composition to which it is compared.

The sweetener composition can have a quantified enhanced sweetness. Such enhanced sweetness may be determined by a sensory test. Examples of sensory taste tests are described herein.

In some instances, a sweetener composition can have the sweetness enhanced by at least 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control composition. The sweetener composition can have the sweetness enhanced by up to 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control composition. the sweetener composition can have the sweetness enhanced by about 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control composition. For example, the sweetness can be enhanced by 10-80%, 20-70%, or 40-60% relative to a control composition.

Methods of Making Sweetener Compositions

In one instance, a method of producing a sweetener composition comprises: mixing one or more sweetener carbohydrates and/or sweetener polyols with a carrier compound precursor and a catalyst. The catalyst then converts the carrier compound precursor to a carrier compound which then interacts with the sweetener carbohydrates and/or sweetener polyols to form the sweetener composition. The sweetener carbohydrates and/or sweetener polyols, catalyst, and carrier compound precursor can be added simultaneously or sequentially in any order. In one example, the sweetener carbohydrates and/or sweetener polyols is first mixed with the carrier compound precursor and then the catalyst is added. In another example, the sweetener carbohydrates and/or sweetener polyols is first mixed with the catalyst and then the carrier compound precursor is added.

The mixing can be accomplished by one or more methods including stirring, grinding, compressing, blending, agitating, rotational mixing, solid-solid mixing with a static mixer, mortar and pestle, Kenics mixing, drum tumbling, and Turbula mixing.

Once the sweetener composition is generated, it is optional to remove the catalyst and/or unregenerated catalyst. This can be accomplished through various means including filtration to remove an ion exchange resin. However, this is optional and in some cases, the catalyst and/or unregenerated catalyst is not removed.

In some cases, the carrier compound precursor is a silicate and the catalyst is an acid. In some cases, the carrier compound precursor is a silicate and the catalyst is an ion exchange resin. In some cases, the carrier compound precursor is a silicate and the catalyst is a cation exchange resin.

In some cases, the carrier compound precursor is sodium silicate and the catalyst is an acid. In some cases, the carrier compound precursor is sodium silicate and the catalyst is an ion exchange resin. In some cases, the carrier compound precursor is sodium silicate and the catalyst is a cation exchange resin.

In some cases, the carrier compound precursor is silicic acid and the catalyst is an acid. In some cases, the carrier compound precursor is silicic acid and the catalyst is a base. In some cases, the carrier compound precursor is silicic acid and the catalyst is an ion exchange resin.

In some cases, a sweetener composition is produced by mixing or dissolving one or more sweetener carbohydrates and/or sweetener polyols, carrier compound precursor, and/or catalyst in a solvent.

The above individual components or reagents may be mixed or dissolved in the same or different solvents. A carrier compound precursor, a catalyst, a solvent, and one or more sweetener carbohydrates and/or sweetener polyols can be mixed together in any order, separately, alternately, simultaneously, or a combination thereof.

Each of the one or more sweetener carbohydrates and/or sweetener polyols, carrier compound precursor, and catalyst may be mixed with a solvent in any order separately, alternately, simultaneously, or a combination thereof (e.g., mixing one or more sweetener carbohydrates and/or sweetener polyols with a solvent and then adding a carrier compound precursor and a catalyst; mixing a carrier compound precursor with a solvent and then adding a catalyst and one or more sweetener carbohydrates and/or sweetener polyols; mixing a catalyst with a solvent and then adding a carrier compound precursor and one or more sweetener carbohydrates and/or sweetener polyols; mixing one or more sweetener carbohydrates and/or sweetener polyols and a carrier compound precursor with a solvent and then adding a catalyst; or mixing one or more sweetener carbohydrates and/or sweetener polyols and a catalyst with a solvent and then adding a carrier compound precursor).

For example, the carrier compound silica can be formed in situ by reacting a carrier compound precursor such as sodium silicate with an acid in a solution of sweetener carbohydrate and/or sweetener polyol in water. Silicic acid is produced by the acidification of silicate in aqueous solution. Condensation of silicic acid produces silica. In some cases, the silica precipitates out of solution. In some cases, the silica remains dissolved in solution. In some cases, the silica does not precipitate. In some cases, the silica is dispersed in solution. The production of silica in situ in the presence of sweetener forms associations between the silica and sweetener, e.g., through hydrogen bonding.

During mixing, one or more reaction parameters such as temperature, concentration, stoichiometry, reaction time, order of mixing, mixing speed, mixing time, and pH can be adjusted. Adjusting one or more reaction parameters may affect the molecular structure, porosity, density, and/or particle size of the carrier compound that is formed.

The concentration of one or more sweetener carbohydrates and/or sweetener polyols mixed or dissolved in a solvent can be adjusted. The concentration of one or more sweetener carbohydrates and/or sweetener polyols mixed or dissolved in a solvent may be at least 5%, 10%, 15%, 20%, 25%, 30%, 35%, 40%, 45%, 50%, 55%, 60%, 65%, 70%, 75%, 80%, 85%, 90%, or 95% by weight. The concentration of one or more sweetener carbohydrates and/or sweetener polyols mixed or dissolved in a solvent may be up to 5%, 10%, 15%, 20%, 25%, 30%, 35%, 40%, 45%, 50%, 55%, 60%, 65%, 70%, 75%, 80%, 85%, 90%, or 95% by weight. The concentration of one or more sweetener carbohydrates and/or sweetener polyols mixed or dissolved in a solvent may be about 5%, 10%, 15%, 20%, 25%, 30%, 35%, 40%, 45%, 50%, 55%, 60%, 65%, 70%, 75%, 80%, 85%, 90%, or 95% by weight. In some cases, the concentration of one or more sweetener carbohydrates and/or sweetener polyols mixed or dissolved in a solvent is between about 10-70%, 15-70%, 15-65%, 20-65%, 20-60%, 20-50%, 20-40%, or 20-30%. In some cases, the concentration of one or more sweetener carbohydrates and/or sweetener polyols mixed or dissolved in a solvent is about 20%. In some cases, the concentration of one or more sweetener carbohydrates and/or sweetener polyols mixed or dissolved in a solvent is about 30%. In some cases, the concentration of one or more sweetener carbohydrates and/or sweetener polyols mixed or dissolved in a solvent is about 65%.

The stoichiometry of the catalyst relative to the carrier compound precursor, carrier compound precursor counterion, or hydroxide ion can be adjusted. The stoichiometry or molar ratio of the catalyst relative to the carrier compound precursor, carrier compound precursor counterion, or hydroxide ion may be at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, or 10.0. The stoichiometry or molar ratio of the catalyst relative to the carrier compound precursor, carrier compound precursor counterion, or hydroxide ion may be up to 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, or 10.0. The stoichiometry or molar ratio of the catalyst relative to the carrier compound precursor, carrier compound precursor counterion, or hydroxide ion may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, or 10.0. The stoichiometry or molar ratio of the catalyst relative to the carrier compound precursor, carrier compound precursor counterion, or hydroxide ion may be between 0.1-5.0, 0.1-1.0, 1.0-2.0, 2.0-3.0, 3.0-4.0, 4.0-5.0, 0.1-2.0, 1.0-3.0, 2.0-4.0, 3.0-5.0, 0.1-3.0, 1.0-4.0, 2.0-5.0, 0.1-4.0, or 1.0-5.0. The stoichiometry or molar ratio of the catalyst relative to the carrier compound precursor, carrier compound precursor counterion, or hydroxide ion may be about 1.5.

The reaction temperature can be adjusted. The reaction temperature may be at least 15, 20, 25, 30, 35, 40, 45, 50, 55, 60, 65, 70, 75, 80, or 85° C. The reaction temperature may be up to 15, 20, 25, 30, 35, 40, 45, 50, 55, 60, 65, 70, 75, 80, or 85° C. The reaction temperature may be about 15, 20, 25, 30, 35, 40, 45, 50, 55, 60, 65, 70, 75, 80, or 85° C. The reaction temperature may be room temperature.

The pH of the reaction mixture can be adjusted. The pH of the reaction mixture may be at least 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. The pH of the reaction mixture may be up to 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. The pH of the reaction mixture may be about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0. The pH of the reaction mixture may be between about 2.0-10.0, 2.0-9.0, 2.0-8.0, 2.0-7.0, 2.0-6.0, 2.0-5.0, 2.0-4.0, 3.0-10.0, 4.0-10.0, 5.0-10.0, 6.0-10.0, 7.0-10.0, 8.0-10.0, 9.0-10.0, 3.0-9.0, 4.0-9.0, 5.0-9.0, 6.0-9.0, 7.0-9.0, 8.0-9.0, 3.0-8.0, 3.0-7.0, 3.0-6.0, 3.0-5.0, 3.0-4.0, 6.0-8.0, 6.0-7.0, or 7.0-8.0. The pH of the reaction mixture may be about 8.5. The pH of the reaction mixture may be about 7.0.

The reaction of a carrier compound precursor with a catalyst to form a carrier compound may or may not go to completion. In some cases, the reaction goes to completion. In some cases, the reaction does not go to completion. In some cases, about 10%, 20%, 30%, 40%, 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% of the carrier compound precursor is reacted to form carrier compound. In some cases, up to 10%, 20%, 30%, 40%, 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% of the carrier compound precursor is reacted to form carrier compound. In some cases, at least 10%, 20%, 30%, 40%, 50%, 60%, 70%, 80%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% of the carrier compound precursor is reacted to form carrier compound.

Formulations of Sweetener Compositions

A sweetener composition may be formulated as a syrup. In some cases, the ratio of total sweetener carbohydrates and/or sweetener polyols to solvent in a sweetener composition formulation is at least 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. In some cases, the ratio of total sweetener carbohydrates and/or sweetener polyols to solvent in a sweetener composition formulation is up to 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. In some cases, the ratio of total sweetener carbohydrates and/or sweetener polyols to solvent in a sweetener composition formulation is about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5.

The sweetener compositions herein can be added to or mixed with one or more food additives. Food additives can add volume and/or mass to a sweetener composition. The sweetener compositions herein may be mixed with food additives such that up to 0.001, 0.005, 0.01, 0.05, 0.1, 0.5, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99 weight % of the sweetener composition formulation is food additives. The sweetener compositions herein may be mixed with food additives such that at least 0.001, 0.005, 0.01, 0.05, 0.1, 0.5, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99 weight % of the sweetener composition formulation is food additives. The sweetener compositions herein may be mixed with food additives such that about 0.001, 0.005, 0.01, 0.05, 0.1, 0.5, 1, 1.5, 2, 2.5, 3, 3.5, 4, 4.5, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, or 99 weight % of the sweetener composition formulation is food additives. Some non-limiting examples of a food additive include food coloring, natural flavoring, artificial flavoring, batch marker, food stabilizer, food acid, filler, anticaking agent, antioxidant, bulking agent, color retention agent, emulsifier, humectant, thickener, pharmaceutical excipient, solid diluent, acid salt, alkali salt, organic salt, inorganic salt, nutrient (e.g., macronutrient, micronutrient, essential nutrient, non-essential nutrient, dietary fiber, amino acid, vitamin, dietary mineral), sweetener, artificial sweetener, natural sugar substitute, and preservative, for example. Some non-limiting examples of food additives are silica, silicon dioxide, cellulose, microcrystalline cellulose, powdered cellulose, starch, modified food starch, amylum, calcium carbonate, maltodextrin, hemicellulose, cyclodextrins, hydroxyalkyl cyclodextrins, inulin, pectin, chitin, chitosan, carrageenans, agar, natural gums (e.g., gum arabic, gellan gum, guar gum, locust bean gum, and xanthan gum), and magnesium stearate. Some non-limiting examples of an artificial sweetener are acesulfame potassium, advantame, alitame, aspartame, sodium cyclamate, dulcin, glucin, neohesperidin dihydrochalcone, neotame, P-4000, saccharin, aspartame-acesulfame salt, and sucralose. Some non-limiting examples of natural sugar substitutes are brazzein, curculin, glycyrrhizin, glycerol, inulin, mogroside, mabinlin, malto-oligosaccharide, mannitol, miraculin, monatin, monellin, osladin, pentadin, stevia (including partly stevia components), tagatose, and thaumatin. In some cases, a food additive may be a byproduct of the method of making a sweetener composition. For instance, a food additive may be a carrier compound precursor, a carrier compound precursor counterion, a catalyst, and/or an unregenerated catalyst. In some cases, a food additive may be a conjugate acid salt of a catalyst base or conjugate base salt of a catalyst acid. In some cases, a food additive differs from a sweetener carbohydrate or sweetener polyol, as food additives do not coat the carrier compound. In some cases, a compound can function as one or more of a carrier compound, a food additive, and a sweetener carbohydrate or sweetener polyol. A food additive may be a combination of two or more distinct food additives. In some cases, the sweetener composition and/or sweetener composition formulation does not comprise DNA, protein, lignin, and/or magnetic particles.

At least 5, 10, 15, 20, 25, 30, 35, 40, 45, 50, 55, 60, 65, 70, 75, 80, 85, 90, 95, 96, 97, 98, 99, 99.5, 99.9, or 100% of the sweetener composition formulation by weight may be one, two, three, four, or five components selected from the group consisting of sweetener carbohydrate, sweetener polyol, carrier compound, solvent, and food additive. Up to 5, 10, 15, 20, 25, 30, 35, 40, 45, 50, 55, 60, 65, 70, 75, 80, 85, 90, 95, 96, 97, 98, 99, 99.5, 99.9, or 100% of the sweetener composition formulation by weight may be one, two, three, four, or five components selected from the group consisting of sweetener carbohydrate, sweetener polyol, carrier compound, solvent, and food additive. About 5, 10, 15, 20, 25, 30, 35, 40, 45, 50, 55, 60, 65, 70, 75, 80, 85, 90, 95, 96, 97, 98, 99, 99.5, 99.9, or 100% of the sweetener composition formulation by weight may be one, two, three, four, or five components selected from the group consisting of sweetener carbohydrate, sweetener polyol, carrier compound, solvent, and food additive.

Methods of Making and/or Formulating Sweetener Compositions and/or Sweetener Composition Formulations A method of making and/or formulating a sweetener composition and/or sweetener composition formulation may comprise drying and/or concentrating. In some cases, drying forms a dry and/or dehydrated sweetener composition and/or sweetener composition formulation. In some cases, drying forms a solid sweetener composition and/or sweetener composition formulation. In some cases, concentrating forms a concentrated sweetener composition and/or sweetener composition formulation. Some non-limiting examples of drying methods include thermal drying, evaporation, distillation, boiling, heating in an oven, vacuum drying, spray drying, freeze drying, lyophilization, or a combination thereof. The mechanism of drying can affect the hydration and molecular structure of the sweetener composition and/or formulation thus giving rise to sweetener compositions and/or formulations with different physical properties. The sweetener composition and/or sweetener composition formulation can be dried until the composition and/or formulation comprises up to 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, or 80% solvent (e.g., water) by weight. The sweetener composition and/or sweetener composition formulation can be dried until the composition and/or formulation comprises at least 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, or 80% solvent (e.g., water) by weight. The sweetener composition and/or sweetener composition formulation can be dried until the composition and/or formulation comprises about 0.001, 0.005, 0.01, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, or 80% solvent (e.g., water) by weight. For example, a sweetener composition formulated as a syrup can be dried via any standard drying method (e.g., 12-80 hours in an oven at 60° C.) to remove a solvent to form a dry solid sweetener composition and/or sweetener composition formulation. In another example, a sweetener composition formulated as a syrup can be concentrated (e.g., from a syrup with 80% water to a syrup with 35% water).

A method of making and/or formulating a sweetener composition and/or sweetener composition formulation may comprise diluting and/or hydrating. In some cases, the diluting may comprise addition of a solvent. The sweetener composition and/or sweetener composition formulation can be diluted until the composition and/or formulation comprises up to 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99, 99.5, or 99.9% water by weight. The sweetener composition and/or sweetener composition formulation can be diluted until the composition and/or formulation comprises at least 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99, 99.5, or 99.9% water by weight. The sweetener composition and/or sweetener composition formulation can be diluted until the composition and/or formulation comprises around 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 96, 97, 98, 99, 99.5, or 99.9% water by weight. For example, a sweetener composition formulated as a syrup can be diluted (e.g., from a syrup with 35% water to a syrup with 80% water). In another example, a dry sweetener composition can be hydrated (e.g., from a dry solid to a syrup with 80% water).

A method of making and/or formulating a sweetener composition and/or sweetener composition formulation may comprise mechanical mixing or grinding. A sweetener composition, sweetener composition formulation, individual component (e.g., sweetener carbohydrate, sweetener polyol), individual reagent (e.g., carrier compound precursor, catalyst), intermediate, and/or reaction mixture can be mixed or ground by one or more mechanical methods. Non-limiting examples of mechanical methods include stirring, grinding, compressing, blending, agitating, rotational mixing, solid-solid mixing with a static mixer, mortar and pestle, Kenics mixing, drum tumbling, and Turbula mixing. In some cases, two or more forms of mechanical methods can be used in series or in parallel. For example, a sweetener composition and/or sweetener composition formulation can be ground mechanically in a grinder and subsequently further ground mechanically via mortar and pestle. The conditions of the mechanical coating or grinding (e.g., temperature, time duration, speed, timing, rate, force, pressure, etc.) can affect the sweetness of the resulting composition and/or formulation. These conditions may be selected to give the largest enhancement of sweetness to the resulting composition and/or formulation. Mixing or grinding may be carried out for at least 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. Mixing or grinding may be carried out for up to 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. Mixing or grinding may be carried out for about 0.1, 0.2, 0.3, 0.4, 0.5, 1.0, 2.0, 3.0, 4.0, 5.0, 6.0, 7.0, 8.0, 9.0, 10.0, 12.0, 14.0, 16.0, 18.0, or 20.0 min. In some cases when two or more forms of mechanical methods are used in series or in parallel, the timing and conditions of each form can be selected independently.

A method of making and/or formulating a sweetener composition and/or sweetener composition formulation may comprise sonicating. A sweetener composition, sweetener composition formulation, individual component (e.g., sweetener carbohydrate, sweetener polyol), individual reagent (e.g., carrier compound precursor, catalyst), intermediate, and/or reaction mixture can be subjected to sonication. The sonication can be for up to 1, 2, 3, 4, 5, 6, 7, 8, 9, 10, 12, 14, 16, 20, 24, 30, 40, 50, or 60 min. The sonication can be for at least 1, 2, 3, 4, 5, 6, 7, 8, 9, 10, 12, 14, 16, 20, 24, 30, 40, 50, or 60 min. The sonication can be for about 1, 2, 3, 4, 5, 6, 7, 8, 9, 10, 12, 14, 16, 20, 24, 30, 40, 50, or 60 min. The sonication may occur with heating. The sonication may occur at a temperature of up to 25, 30, 35, 40, 45, 50, 55, 60, 65, 70, 75, 80, 85, 90, 95, or 100° C. The sonication may occur at a temperature of at least 25, 30, 35, 40, 45, 50, 55, 60, 65, 70, 75, 80, 85, 90, 95, or 100° C. The sonication may occur at a temperature of around 25, 30, 35, 40, 45, 50, 55, 60, 65, 70, 75, 80, 85, 90, 95, or 100° C. The sonication may occur at room temperature. In some cases, the sonication occurs during grinding or mixing. In some cases, the sweetener composition and/or sweetener composition formulation is sonicated. In some cases, the sweetener composition and/or sweetener composition formulation is not sonicated.

A method of making and/or formulating a sweetener composition and/or sweetener composition formulation may comprise filtering and/or sieving. A sweetener composition, sweetener composition formulation, individual component (e.g., sweetener carbohydrate, sweetener polyol), individual reagent (e.g., carrier compound precursor, catalyst), intermediate, and/or reaction mixture can be passed through a sieve or sieving tower to remove particles of particular sizes, of at least a minimum size, of at most a maximum size, or of at least a minimum size and at most a maximum size from the composition. The sieve can have a mesh with openings up to 30, 40, 50, 60, 70, 80, 90, 100, 110, 120, 130, 140, 150, 160, 170, 180, 190, or 200 mesh. The sieve can have a mesh with openings of at least 30, 40, 50, 60, 70, 80, 90, 100, 110, 120, 130, 140, 150, 160, 170, 180, 190, or 200 mesh. The sieve can have a mesh with openings around 30, 40, 50, 60, 70, 80, 90, 100, 110, 120, 130, 140, 150, 160, 170, 180, 190, or 200 mesh. The sieve can have a mesh with openings of about 40 to about 100 mesh. The sieve can have a mesh with openings of about 60 to about 70 mesh.

A method of making and/or formulating a sweetener composition and/or sweetener composition formulation may comprise isolating or purifying. In some cases, the method comprises removing a portion of the unreacted carrier compound precursor. In some cases, the method comprises removing a portion of the carrier compound precursor counterion. In some cases, the method comprises removing a portion of the catalyst. In some cases, the method comprises removing a portion of the unregenerated catalyst.

Applications of Sweetener Compositions

A sweetener composition provided herein may be used as a sweetener for a consumable product. A consumable product may comprise a composition provided herein. Some non-limiting examples of a consumable product include food products, beverage products, pharmaceutical products, and hygiene products.

The consumable product may contain silica. The consumable product may contain up to 0.0001, 0.0005, 0.001, 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% silica weight/weight. The consumable product may contain at least 0.0001, 0.0005, 0.001, 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% silica weight/weight. The consumable product may contain about 0.0001, 0.0005, 0.001, 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0% silica weight/weight.

The consumable product may have an acidic pH. In some cases, the consumable product may have a pH of at least 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9. In some cases, the consumable product may have a pH of up to 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9. In some cases, the consumable product may have a pH of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9.

A method of producing a consumable product with enhanced sweetness, lower caloric value, reduced bitterness, or a combination thereof may comprise adding a sweetener composition and/or sweetener composition formulation to the consumable product or substituting a portion of one or more sweetener ingredients in the consumable product with a sweetener composition and/or formulation. The sweetener composition and/or formulation may reduce the perceived bitterness of a consumable product. The sweetener compositions and/or formulations described herein can function as bitterness reducers and, in some instances, as bitterness masking agents. For example, adding a sweetener composition and/or formulation described herein to a consumable product can reduce or mask a bitter taste. A sweetener composition and/or formulation as described herein can reduce the bitterness of a medicine or pharmaceutical. For example, a method of reducing bitterness in a medicine or pharmaceutical can comprise adding a sweetener composition and/or formulation described herein to the medicine or pharmaceutical. Reducing the bitterness of a medicine can have the beneficial effect of increasing patient compliance and desire to take a medicine, particularly with pediatric patients. In some cases, a consumable product may comprise one or more modifying components that allow for incorporation of the sweetener composition and/or formulation.

A sweetener composition and/or sweetener composition formulation described herein can be added to or substituted into (e.g., by replacing a portion of one or more sweetener ingredients in the consumable product) a consumable product to produce at least 1, 2, 3, 4, 5, 6, 7, or 8; up to 1, 2, 3, 4, 5, 6, 7, or 8; or about 1, 2, 3, 4, 5, 6, 7, or 8 of the characteristics selected from the group consisting of increased sweetness, reduction of sweetener used while maintaining sweetness sensation, increased creamy aftertaste, decreased bitter aftertaste, decreased mouth drying aftereffect, decreased metallic aftertaste, decreased liquorice aftertaste, and reduced caloric value of the consumable product. The characteristic of the consumable product comprising the sweetener composition and/or formulation can be compared to a control product that does not have the sweetener composition and/or formulation added to it or substituted into it. For example, a consumable product with an added or substituted sweetener composition and/or formulation can have one or more of the characteristics enhanced by at least 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control product. A consumable product with an added or substituted sweetener composition and/or formulation can have one or more of the characteristics enhanced by up to 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control product. A consumable product with an added or substituted sweetener composition and/or formulation can have one or more of the characteristics enhanced by about 5%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, or 300% relative to a control product. For example, the sweetness can be enhanced by 10-80%, 20-70%, or 40-60% relative to a control product.

Sensory Testing

Enhanced sweetness can be determined by a sensory test. Equivalent sweetness with a lower caloric value can be determined by a sensory test. The sensory test may be a taste test. The sensory test may be a blind test. One non-limiting example of a taste test method to measure enhanced sweetness is to taste a set amount of a control composition, and then taste varying amounts of the sweetener composition to find the amount of sweetener composition that corresponds to the sweetness of the control composition. The enhanced sweetness can be calculated by the following formula: [amount of control composition−amount of sweetener composition required for equal sweetness]/[amount of control composition]. For example, varying amounts of a sweetener composition described herein (e.g., 5, 4, 3, 2 and 1 mg of a composition comprising 65% sucrose and 1% silica) are tasted to find an equal sweetness to a control composition (e.g., 5 mg sucrose). In this case, if the test shows that 3 mg of the sweetener composition has an equivalent sweetness to 5 mg of the control composition, then the enhanced sweetness is calculated as (5-3)/5=40%.

A sensory test can use one or more various protocols. For example, a sensory test can be the "triangle method", follow ISO requirements, or a combination thereof. The taste test can be the average of multiple trials. For example, each taste tester can consume multiple sweetener compositions or foods, beverages, or consumable products comprising a sweetener composition and sequence them by relative sweetness. A taste test can comprise tasting a standard and determining whether a tested composition is more or less sweet than the standard.

A taste test may be a screening test, a professional taste test, or a market research test. A screening test may be performed by at least 1, 2, 3, 4, 5, 6, 7, 8, or 9 taste testers. A professional taste test may be performed by at least 10, 15, 20, 25, or 30 taste testers. A market research test may be performed by at least 31, 40, 50, 60, 70, 80, 90, 100, 150, 200, 300, 400, or 500 taste testers. A taste tester can be a person with average taste perception. A taste tester can be a professional taste tester. A taste tester can be a person who has passed a tasting exam by correctly identifying foods or food components. A taste tester can be a person who can identify the relative amounts of a taste or flavor (e.g., correctly sequence varying amounts of sugar in water).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Formation of a Sweetener Composition Using Silicate and Ion Exchange Resin A) 1% Silica Weight/Weight:

A stock solution is prepared by adding 2.45 grams of an aqueous solution of sodium silicate (Sigma Aldrich, 26.5% $SiO_2$, 10.6% $Na_2O$, weight/weight) to 100 grams of an aqueous sucrose solution (65% weight/weight). The solutions are mixed thoroughly to ensure complete mixing. To a portion of the stock solution (20.4 gram) are added 5.0 grams of a strong acid ion exchange resin (Purolite SST C60H, total capacity 4 eq/1 kg). The resulting suspension is stirred gently so as not to harm the resin beads. The pH is monitored for 35 minutes (pH=9) and 5.0 additional grams of the strong acid ion exchange resin (Purolite SST C60H, total capacity 4 eq/1 kg) are added. After an additional 20 minutes, the pH of the solution reaches 7, and the mixture is filtered to remove the resin. The remaining filtrate liquid, 1A, is isolated. Initial taste test indicates slight sweetness. A portion of 1A is dried in an oven to remove water and to produce a solid sweetener composition, 1A-2.

Example 2: Formation of a Sweetener Composition Using Different Percentages of Silicate and Ion Exchange Resin with Sonication 65% sucrose solution is prepared by dissolving sucrose in water. Sodium silicate is added to the sucrose solution in appropriate amounts to obtain desired silica percentage. 1.5 equivalents of Dowex 88(H) resin are added. Samples are prepared with or without sonication during ion exchange at 40° C. Final pH of about 8.5 is obtained.

| Description | sucrose [gr ± 0.1 mg] | Distilled deionized water [gr ± 0.1 mg] | Sodium silicate [μL ± 1 μL] | DOWEX 88(H) [gr ± 0.1 mg] |
|---|---|---|---|---|
| 0.1% silica | 32.5 | 17.5 | 90 | 0.36 |
| 0.2% silica | 32.5 | 17.5 | 185 | 0.72 |
| 0.5% silica | 32.5 | 17.15 | 445 | 1.8 |
| 1% silica | 32.5 | 16.75 | 890 | 3.6 |

Example 3: Formation of a Sweetener Composition with Sonication pH measurements are taken of samples prepared in Example 2.

| | 0.1% silica | | 0.2% silica | | 0.5% silica | | 1% silica | |
|---|---|---|---|---|---|---|---|---|
| | No Sonication | Sonication | No Sonication | Sonication | No Sonication | Sonication | No Sonication | Sonication |
| Time to obtain pH ~8.5 [min] | 100-120 | 95 | 80 | 50 | 40 | 27 | 30 | 20 |

Example 4: Formation of a Sweetener Composition by Mixing Sucrose Solution with Resin Before Adding Silicate 65% sucrose solution is prepared by dissolving sucrose in water. 1.5 equivalents of Dowex 88(H) resin in reference to sodium ions are added. Mixture temperature is kept at 40° C. Sodium silicate is added to the mixture in appropriate amounts to obtain desired silica percentages of 0.1% and 0.2% in reference to sucrose, and ion exchange takes place. Final pH of about 8.5 is obtained.

| | 0.1% silica | | 0.2% silica | |
|---|---|---|---|---|
| | Resin inserted after sodium silicate | Resin inserted prior to sodium silicate | Resin inserted after sodium silicate | Resin inserted prior to sodium silicate |
| Time to obtain pH~8.5 [min] | 100-120 | 70 | 80 | 60 |

Example 5: Formation of a Sweetener Composition Using Different Ion Exchange Resin Equivalents 65% sucrose solution is prepared by dissolving sucrose in water. Sodium silicate is added to the sucrose solution in appropriate amounts to obtain desired silica percentages of 0.1% and 0.2% in reference to sucrose. 1-5 equivalents of Dowex 88(H) resin are added at 40° C. and ion exchange takes place. Final pH of about 8.5 is obtained.

| | 0.1% silica | | | | | 0.2% silica | | | | |
|---|---|---|---|---|---|---|---|---|---|---|
| | 1 eq. resin | 1.5 eq. resin | 2 eq. resin | 3 eq. resin | 5 eq. resin | 1 eq. resin | 1.5 eq. resin | 2 eq. resin | 3 eq. resin | 5 eq. resin |
| Time to obtain pH ~8.5 [min] | 190 | 120 | 85 | 45 | 25 | 190 | 80 | 70 | 40 | 20 |

Example 6: Formation of a Sweetener Composition Using Different Temperature During Ion Exchange 65% sucrose solution is prepared by dissolving sucrose in water. Sodium silicate is added to the sucrose solution in appropriate amount to obtain desired silica percentage of 0.1% in reference to sucrose. 1.5 equivalents of Dowex 88(H) resin are added at differing temperatures and ion exchange takes place at different exchange temperatures. Final pH of about 8.5 is obtained.

| | Room temperature | 40° C. | 60° C. | 75° C. |
|---|---|---|---|---|
| Time to obtain pH~8.5 [min] | 200 | 120 | 30 | 10 |

Example 7: Formation of a Sweetener Composition Using Silicate and Citric Acid

65% sucrose solution is prepared. Sodium silicate is added in appropriate amounts to obtain desired silica percentage. 1.5 equivalents of citric acid are added relative to the number of moles of hydroxide ions. pH measurements are taken, with stable pH measurements after 10 minutes. Samples are prepared at room temperature.

| Description | Sucrose [gr ± 0.1 mg] | Deionized water [gr ± 0.1 mg] | Sodium silicate [μL ± 1 μL] | Citric acid [gr ± 0.1 mg] | Final pH level |
|---|---|---|---|---|---|
| 0.2% silica with 1.5 eq. citric acid | 32.5019 | 17.5044 | 185 | 0.2454 | 3.34 |

-continued

| Description | Sucrose [gr ± 0.1 mg] | Deionized water [gr ± 0.1 mg] | Sodium silicate [µL ± 1 µL] | Citric acid [gr ± 0.1 mg] | Final pH level |
|---|---|---|---|---|---|
| 2% silica with 1.5 eq. citric acid | 32.5016 | 16.0037 | 1790 | 2.4491 | 3.13 |

Example 8: Formation of a Sweetener Composition Using Silicate and Different Equivalents of Citric Acid 65% sucrose solution is prepared. Sodium silicate is added in appropriate amounts to obtain 0.1% silica. 0.33, 0.5, 1.0, 1.2, 1.5, 2.0, or 5.0 equivalents of citric acid are added. Samples are prepared at room temperature.

| Description | 65% sucrose syrup [gr ± 0.1 mg] | Sodium silicate [µL ± 1 µL] | Citric acid [gr ± 0.1 mg] |
|---|---|---|---|
| 0.1% silica with 0.33 eq. citric acid | 50.0340 | 90 | 0.0272 |
| 0.1% silica with 0.5 eq. citric acid | 45.0772 | 90 | 0.0368 |
| 0.1% silica with 1 eq. citric acid | 100.0755 | 175 | 0.1635 |
| 0.1% silica with 1.2 eq. citric acid | 100.0677 | 175 | 0.1961 |
| 0.1% silica with 1.5 eq. citric acid | 100.0507 | 175 | 0.2449 |
| 0.1% silica with 2 eq. citric acid | 50.0561 | 90 | 0.1635 |
| 0.1% silica with 5 eq. citric acid | 50.0587 | 90 | 0.4090 |

Example 9: Formation of a Sweetener Composition Using Silicate and Phosphoric Acid 65% sucrose solution is prepared. Sodium silicate is added in appropriate amounts to obtain desired silica percentage. 2 molar stock solution of phosphoric acid is added to obtain 0.5, 1, or 2 equivalents relative to the number of moles of hydroxide ions. pH measurements are taken, with stable pH measurements after 10 minutes. Samples are prepared at room temperature.

| Silica percentage | Phosphoric acid molar equivalences | 65% sucrose solution [gr ± 0.1 mg] | Sodium silicate [µL ± 1 µL] | Phosphoric acid, 2M µL ± 1 µL] |
|---|---|---|---|---|
| 0.1% | 0.5 | 50.0057 | 90 | 53 |
|  | 1 | 50.0029 | 90 | 106 |
|  | 2 | 50.0050 | 90 | 212 |
| 0.2% | 0.5 | 50.0170 | 180 | 106 |
|  | 1 | 50.0040 | 180 | 212 |
|  | 2 | 50.0054 | 180 | 424 |

Example 10: Formation of a Sweetener Composition Using Different Concentrations of Sucrose Solution 10.6%, 20%, and 30% sucrose solutions are prepared. Sodium silicate is added in appropriate amounts to obtain 0.2% silica relative to sucrose (w/w). 1.5 equivalents of Dowex 88(H) resin are added. Samples are prepared at 40° C. Final pH of about 7.0 is obtained.

| Sucrose solution | Sucrose [gr ± 0.1 mg] | Deionized water [gr ± 0.1 mg] | Sodium silicate [µL ± 1 µL] | Dowex resin [gr ± 0.1 mg] | Time to obtain pH~7 |
|---|---|---|---|---|---|
| 30% | 15.0081 | 35.0065 | 85 (=0.1198 gr) | 0.3341 | 30 |
| 20% | 9.9979 | 39.9979 | 55 (=0.0754 gr) | 0.2201 | 29 |
| 10.6% | 5.3008 | 44.7067 | 30 (=0.0400 gr) | 0.1174 | 34 |

Sweetener compositions prepared from 20%, 30%, and 65% sucrose solution are diluted to 10.6% sucrose.

|  | 10.6% sucrose | Sweetener composition prepared from 10.6% sucrose | Sweetener composition prepared from 20% sucrose | Sweetener composition prepared from 30% sucrose | Sweetener composition prepared from 65% sucrose |
|---|---|---|---|---|---|
| Taster 1 | X | 0.75 | 1 | 0.5 | −0.25 |
| Taster 2 | X | 0.25 | 0.5 | 0.5 | −0.25 |
| Taster 3 | X | 0.5 | 1 | 0.25 | 1 |
| Taster 4 | X | −0.5 | 0.5 | 0.25 | 0.25 |
| Taster 5 | X | 0 | 0.5 | 1 | 0 |
| Taster 6 | X | 0.25 | −0.25 | 0.25 | 0.5 |
| Average | X | 0.21 | 0.54 | 0.56 | 0.21 |

Key:
X represents a level of sweetness,
X − 0.25 represents a taste that is less sweet than X,
X − 0.5 represents a taste that is less sweet than X − 0.25,
X + 0.25 represents a taste that is more sweet than X,
X + 0.5 represents a taste that is more sweet than X + 0.25,
X + 0.75 represents a taste that is more sweet than X + 0.5,
X + 1 represents a taste that is more sweet than X + 0.75

Example 11: Formation of a Sweetener Composition Comprising Glucose

65% glucose solution is prepared. Sodium silicate is added in appropriate amounts to obtain 0.2% silica relative to glucose (w/w). 1.5 equivalents of Dowex 88(H) resin are added. Samples are prepared at 40° C. Final pH of about 7.0 is obtained.

| Sugar | Sugar weight [gr ± 0.1 mg] | Distilled deionized water [gr ± 0.1 mg] | Sodium silicate [µL ± 1 µL] | Measured pH prior to resin insertion | DOWEX 88(H) [gr ± 0.1 mg] | Time to obtain pH ~7 [min] |
|---|---|---|---|---|---|---|
| Glucose | Glucose monohydrate; 35.7475 | 14.2453 | 185 | 8.7 | 0.7253 | 65 |

|  | 10.6% Glucose | Sweetener composition, 10.6% glucose | Sweetener composition, 10.6% glucose |
| --- | --- | --- | --- |
| Taster 1 | X | X + 0.5 | X + 0.5 |
| Taster 2 | X | X + 1 | X + 0.5 |
| Taster 3 | X | X + 1 | X + 1 |
| Taster 4 | X | X + 0.5 | X + 0 |
| Taster 5 | X | X + 0.5 | X + 0.5 |
| Average | X | X + 0.7 | X + 0.5 |

Key:
X represents a level of sweetness,
X + 0.5 represents a taste that is more sweet than X,
X +1 represents a taste that is more than x + 0.5

Example 12: Formation of a Sweetener Composition Comprising Fructose

65% fructose solution is prepared. Sodium silicate is added in appropriate amounts to obtain 0.2% silica relative to fructose (w/w). 1.5 equivalents of Dowex 88(H) resin are added. Samples are prepared at 40° C. Final pH of about 7.0 is obtained.

| Sugar | Sugar weight [gr ± 0.1 mg] | Distilled deionized water [gr ± 0.1 mg] | Sodium silicate [µL ± 1 µL] | Measured pH prior to resin insertion | DOWEX 88(H) [gr ± 0.1 mg] | Time to obtain pH ~7 [min] |
| --- | --- | --- | --- | --- | --- | --- |
| Fructose | Crystalline fructose; 32.5019 | 17.5040 | 185 | 7.65 | 0.7266 | 6 |

|  | 10.6% fructose | Sweetener composition, 10.6% fructose | Sweetener composition, 10.6% fructose |
| --- | --- | --- | --- |
| Taster 1 | X | X − 0.25 | X + 1 |
| Taster 2 | X | X | X |
| Taster 3 | X | X − 0.25 | X + 0.25 |
| Taster 4 | X | X + 0.5 | X + 0.25 |
| Taster 5 | X | X + 0.5 | X + 0.5 |
| Average | X | X + 0.1 | X + 0.4 |

Key:
X represents a level of sweetness,
X + 0.25 represents a taste that is more sweet than X,
X + 0.5 represents a taste that is more sweet than X + 0.25,
X + 1 represents a taste that is more sweet than X + 0.5,
X − 0.25 represents a taste that is less sweet than X

Example 13: Formation of a Sweetener Composition Comprising High Fructose Corn Syrup Sodium silicate is added in appropriate amounts to high fructose corn syrup (HFCS F-42) to obtain 0.2% silica relative to total brix or glucose content. 1.5 equivalents of Dowex 88(H) resin are added. Samples are prepared at 40° C. Final pH of about 7.0 is obtained.

| Description | HFCS [gr ± 0.1 mg] | Sodium silicate [µL ± 1 µL] | Dowex resin [gr ± 0.1 mg] | Time to obtain pH~7 [min] |
| --- | --- | --- | --- | --- |
| 0.2% silica in reference to total brix | 50.0063 | 185 | 0.7707 | 53 |

| Description | HFCS [gr ± 0.1 mg] | Sodium silicate [μL ± 1 μL] | Dowex resin [gr ± 0.1 mg] | Time to obtain pH~7 [min] |
|---|---|---|---|---|
| 0.2% silica in reference to glucose | 50.0088 | 110 (=0.1532 gr) | 0.4478 | 25 |

Example 14: Formation of a Sweetener Composition Comprising the Sweetener Polyol Maltitol 65% maltitol solution is prepared. Sodium silicate is added in appropriate amounts to obtain 0.2% silica relative to maltitol (w/w). 1.5 equivalents of Dowex 88(H) resin are added. Samples are prepared at 40° C. Final pH of about 8.5 is obtained.

| Maltitol [gr ± 0.1 mg] | Deionized water [gr ± 0.1 mg] | Sodium silicate [μL ± 1 μL] | Dowex resin [gr ± 0.1 mg] | Time to obtain pH~8.5 [min] |
|---|---|---|---|---|
| 13.0035 | 7.0029 | 72 | 0.2291 | 75 |
| 19.4969 | 10.4991 | 105 | 0.4332 | 56 |

Example 15: Formation of a Sweetener Composition Using Different Percentages of Silicate 65% sucrose solution is prepared. Sodium silicate is added in appropriate amounts to obtain desired silica percentage relative to sucrose (w/w). 1.5 equivalents of Dowex 88(H) resin are added. Samples are prepared at 40° C. Final pH of about 8.5 is obtained.

| % silica | sucrose [gr ± 0.1 mg] | Distilled deionized water [gr ± 0.1 mg] | Sodium silicate [μL ± 1 μL] | DOWEX 88(H) [gr ± 0.1 mg] | Time to obtain pH~8.5 [min] |
|---|---|---|---|---|---|
| 0.05 | 32.5067 | 17.5045 | 45 | 0.1819 | 80 |
| 0.1 | 32.5023 | 17.5002 | 90 | 0.3592 | 85 |
| 0.2 | 32.5079 | 15.5011 | 185 | 0.7220 | 75 |
| 0.3 | 32.5067 | 17.2518 | 265 | 1.0816 | 44 |
| 0.4 | 32.5041 | 17.1988 | 345 | 1.4446 | 40 |
| 0.5 | 32.5046 | 17.1523 | 430 | 1.8075 | 30 |
| 0.6 | 32.5031 | 17.0533 | 525 | 2.1561 | 27 |
| 0.7 | 32.5058 | 16.9555 | 615 | 2.5211 | 22 |
| 0.8 | 32.5043 | 16.9008 | 715 | 2.8872 | 21 |
| 0.9 | 32.5064 | 16.8033 | 740 | 3.2450 | 19 |
| 1 | 32.5085 | 16.7524 | 870 | 3.5930 | 19 |
| 1.5 | 32.4976 | 16.1476 | 1305 | 5.3961 | 14 |
| 2 | 32.4994 | 16.0020 | 1740 | 6.9020 | 12 |

Sweetener compositions are diluted to 10.6% sucrose.

| | 10.6% Sucrose | Sweetener composition 0.2% SiO₂ 10.6% dilution | Sweetener composition 0.3% SiO₂ 10.6% dilution | Sweetener composition 0.4% SiO₂ 10.6% dilution | Sweetener composition 0.6% SiO₂ 10.6% dilution | Sweetener composition 0.7% SiO₂ 10.6% dilution | Sweetener composition 0.8% SiO₂ 10.6% dilution | Sweetener composition 0.9% SiO₂ 10.6% dilution |
|---|---|---|---|---|---|---|---|---|
| Taster 1 | X | X + 1 | X + 1.5 | X + 1 lingering | X + 0.25 | X + 0.75 | X | X + 0.25 |
| Taster 2 | X | X + 0.5 | X + 0.75 | X + 1 | X + 0.75 | X + 0.25 | X + 0.25 different | X + 0.5 |
| Taster 3 | X | X + 1 | X + 0.5 | X + 0.5 | X + 0.75 | X | X + 0.5 | X |
| Taster 4 | X | X + 0.25 | X + 0.75 | X + 1 | X + 0.25 broad | X + 0.25 broad | X + 0.25 broad | X |
| Average | X | X + 0.68 | X + 0.87 | X + 0.87 | X + 0.5 | X + 0.31 | X + 0.25 | X + 0.19 |

Key:
X represents a level of sweetness,
X + 0.25 represents a taste that is more sweet than X,
X + 0.5 represents a taste that is more sweet than X + 0.25,
X + 0.75 represents a taste that is more sweet than X + 0.5,
X + 1 represents a taste that is more sweet than X + 0.75

Example 16: Formation of a Sweetener Composition Using Different Percentages of Silicate 20% sucrose solution is prepared. Sodium silicate is added in appropriate amounts to obtain desired silica percentage relative to sucrose (w/w). 1.5 equivalents of Dowex 88(H) resin are added. Samples are prepared at 40° C. Final pH of about 8.5 is obtained.

| Silica percentage | Sucrose weight [gr ± 0.1 mg] | Distilled deionized water [gr ± 0.1 mg] | Sodium silicate [μL ± 1 μL] | DOWEX 88(H) [gr ± 0.1 mg] | Time to obtain pH~8.5 [min] |
|---|---|---|---|---|---|
| 0.1% | 50.0060 gr of 20% sucrose solution | | 29 | 0.1127 | 17 |
| 0.2% | 50.0100 gr of 20% sucrose solution | | 55 | 0.2216 | 12 |
| 0.3% | 50.0055 gr of 20% sucrose solution | | 84 | 0.3371 | 7 |
| 0.5% | 10.0090 | 39.8909 | 128 | 0.5527 | 7 |
| 0.8% | 10.0052 | 39.8192 | 205 | 0.8847 | 5 |

-continued

| Silica percentage | Sucrose weight [gr ± 0.1 mg] | Distilled deionized water [gr ± 0.1 mg] | Sodium silicate [μL ± 1 μL] | DOWEX 88(H) [gr ± 0.1 mg] | Time to obtain pH~8.5 [min] |
|---|---|---|---|---|---|
| 1% | 10.0053 | 39.7638 | 272 | 1.1063 | 5 |
| 1.5% | 10.0045 | 39.6604 | 403 | 1.6567 | 4 |
| 2% | 10.0034 | 39.5258 | 528 | 2.20 | 3 |

Sweetener compositions are taste tested as 20% sucrose solutions.

| | 20% Sucrose solution | 0.1% silica sweetener composition | 0.2% silica sweetener composition | 0.3% silica sweetener composition | 0.5% silica sweetener composition | 0.8% silica sweetener composition | 1% silica sweetener composition | 1.5% silica sweetener composition | 2% silica sweetener composition |
|---|---|---|---|---|---|---|---|---|---|
| Taster 1 | X | X + 0.25 | X + 0.5 lingering | X + 1 | X + 0.75 | X + 1 | X + 1.5 lingering | X | X + 0.5 |
| Taster 2 | X | X + 0.25 | X + 0.75 | X + 0.5 | X + 1 lingering | X + 0.5 | X + 1.5 lingering | X + 0.25 | X + 0.5 |
| Taster 3 | X | X + 0.25 | X + 0.5 | X + 1 | X + 1 | X + 0.25 | X + 1 lingering | X + 0.5 | X |
| Taster 4 | X | X | X + 0.25 | X + 0.5 | X + 0.5 | X + 0.5 | X + 1 short | X | X |
| Average | X | X + 0.18 | X + 0.5 | X + 0.63 | X + 0.81 | X + 0.56 | X + 1.25 | X + 0.18 | X + 0.25 |

Key:
X represents a level of sweetness,
X + 0.25 represents a taste that is more sweet than X,
X + 0.5 represents a taste that is more sweet than X + 0.25,
X + 0.75 represents a taste that is more sweet than X + 0.5,
X + 1 represents a taste that is more sweet than X + 0.75

Example 17: Formation of a Sweetener Composition Using Different Amounts of Citric Acid and at Different pHs 200 grams of 65% sucrose solution are prepared. Sodium silicate is added in appropriate amounts to 100 grams of sucrose solution obtain desired silica percentage relative to sucrose (w/w). Citric acid is added cumulatively in indicated amounts, with 20 grams of mixture set aside after each addition.

| Silica percentage | Citric acid [gr ± 0.1 mg] | pH level |
|---|---|---|
| 0.05% | 0.0164 | 8.87 |
| | 0.0052 | 8.51 |
| | 0.0082 | 5.84 |
| | 0.0082 | 3.68 |
| 0.1% | 0.0327 | 9.09 |
| | 0.107 | 8.49 |
| | 0.104 | 5.85 |
| | 0.0274 | 3.78 |

Example 18: Dried Sweetener Composition Taste Testing

| | Sucrose | Dried 65% sucrose, 0.1% silica, 40° C. | Dried 65% sucrose, 0.2% silica, 40° C. | Dried 65% sucrose, 0.1% silica, 40° C. | Dried 65% sucrose, 0.1% silica, 60° C. | Dried 65% sucrose, 0.1% silica, 75° C. | Dried 65% sucrose, 0.2% silica, 40° C. | Dried 65% sucrose, 0.2% silica, 60° C. | Dried 65% sucrose, 0.2% silica, 75° C. |
|---|---|---|---|---|---|---|---|---|---|
| Taster 1 | X | X + 0.5 | X + 1 | X + 1 | X + 1 | X + 1 | X + 1.5 | X + 1 | X + 2 |
| Taster 2 | X | X + 0.5 | X + 1 | X + 1 | X + 1 | X | X + 1.5 | X + 0.5 | X + 0.5 |
| Taster 3 | X | X + 1 | X − 1 | X + 1 | X + 1.5 | X | X | X + 1.5 | X − 1 |
| Taster 4 | X | X | X + 0.5 | X + 1.5 | X | X + 1 | X + 2 | X + 1.5 | X + 1 |
| Taster 5 | X | X + 0.5 | X + 1 | X + 2 | X | X | X + 1.5 | X + 1 | X |
| Taster 6 | X | X + 1 | X + 2 | X + 2 | X + 1 | X + 1.5 | X + 2 | X + 2 | X + 1.5 |
| Average | X | X + 0.58 | X + 0.75 | X + 1.42 | X + 0.75 | X + 0.58 | X + 1.42 | X + 1.08 | X + 0.67 |

Key:
X represents a level of sweetness,
X + 0.5 represents a taste that is more sweet than X,
X + 1 represents a taste that is more sweet than X + 0.5,
X + 1.5 represents a taste that is more sweet than X + 1,
X + 2 represents a taste that is more sweet than X + 1.5,
X − 1 represents a taste that is less sweet than X Example 19: Sensory Test Procedure The tests are participated by a panel of taste testers who have been sensory tested in the past. All participants have been trained. The tests are divided into the following 4 segments:
  a) Testing the tasters sensory threshold
  b) Calibration
  c) Sucrose versus sweetener composition tastings—in powder and syrup form
  d) Sucrose versus sweetener composition tastings—powders mixed in a separate medium Tasting process: Tasting stages, excluding calibration, are conducted in the form of a "triangle test": each participant is given three samples marked with random numbers that include two identical samples and one dissimilar sample. Participants are instructed to name the different sample in each set and explain the difference in their opinion.

Participants are given two sets of tests in each tasting, where one test included a single reference sample and the other contained two.

Sensory threshold: Panel participants are given seven triangle tests that included various concentrations of sucrose dissolved in water.

Calibration step: This step is added to the tasting process as another form of tasting the panel's sensory threshold for sweetness. All panel members are given two samples of sucrose marked "A" and "B" the samples were of 4 mg and 5 mg respectively in the purpose of testing the panel's ability to recognize such delicate variations.

The rest of the tests are conducted similarly—each sample is tested with sucrose as reference in two sets of triangle tests.

The present invention may be embodied in other specific forms without departing from the spirit or essential attributes thereof.

What is claimed is:

1. A method of producing a sweetener composition, comprising mixing one or more sweetener carbohydrates, wherein the one or more sweetener carbohydrates are selected from the group consisting of sucrose, glucose, fructose, maltose, lactose, high fructose corn syrup, high maltose corn syrup, and a combination thereof, with a carrier compound precursor and a catalyst such that a reaction between the carrier compound precursor and the catalyst occurs in the presence of the one or more sweetener carbohydrates to form a sweetener composition, wherein the sweetener composition comprises one or more sweetener carbohydrates and 0.05-4% by weight of a carrier compound relative to total sweetener carbohydrate; wherein the carrier compound is silica; wherein the catalyst is a strong or weak acid exchange resin; wherein the sweetener composition has enhanced sweetness compared to a control composition; and wherein the control composition consists of the same contents by identity and quantity as the one or more sweetener carbohydrates.

2. The method of claim 1, further comprising drying the sweetener composition.

3. The method of claim 1, further comprising sonicating the sweetener composition.

4. The method of claim 1, further comprising passing the sweetener composition through a sieve.

5. The method of claim 1, wherein the carrier compound precursor is a silicate.

6. The method of claim 5, wherein the silicate is sodium silicate, potassium silicate, calcium silicate, aluminum silicate, tetramethylammonium silicate, sodium metasilicate, sodium metasilicate hydrate, calcium metasilicate, or a combination thereof.

7. The method of claim 1, wherein the carrier compound precursor is silicic acid.

8. The method of claim 1, wherein the sweetness is enhanced by at least 10%.

9. A method of producing a sweetener mixture, comprising mixing one or more sweetener carbohydrates, wherein the one or more sweetener carbohydrates are selected from the group consisting of sucrose, glucose, fructose, maltose, lactose, high fructose corn syrup, high maltose corn syrup, and a combination thereof, with a carrier compound precursor and a catalyst to form silica such that a reaction between the carrier compound precursor and the catalyst occurs in the presence of the one or more sweetener carbohydrates wherein the sweetener mixture comprises one or more sweetener carbohydrates and 0.05-4% by weight of a carrier compound relative to total sweetener carbohydrate; and wherein the catalyst is a strong or weak acid exchange resin.

10. The method of claim 9, wherein the carrier compound precursor is a silicate.

11. The method of claim 10, wherein the silicate is sodium silicate, potassium silicate, calcium silicate, aluminum silicate, tetramethylammonium silicate, sodium metasilicate, sodium metasilicate hydrate, calcium metasilicate, or a combination thereof.

12. The method of claim 11, wherein the silicate is sodium silicate.

13. The method of claim 9, wherein the carrier compound precursor is silicic acid.

* * * * *